United States Patent [19]
Markowitz

[11] Patent Number: 5,350,513
[45] Date of Patent: Sep. 27, 1994

[54] FLEXIBLE-WALLED ABSORBER

[75] Inventor: James P. Markowitz, Bridgeville, Pa.

[73] Assignee: Calgon Carbon Corporation, Pittsburgh, Pa.

[21] Appl. No.: 907,966

[22] Filed: Jul. 2, 1992

[51] Int. Cl.$^5$ ............................................. B01D 29/13
[52] U.S. Cl. ................... 210/264; 210/283; 210/502.1; 55/372; 96/147; 96/151
[58] Field of Search ............... 210/263, 264, 283, 317, 210/356, 447, 502.1, DIG. 6, DIG. 7; 55/361, 365, 366, 372, 378, 387, DIG. 55, DIG. 33, DIG. 30, 384, 387; 96/147, 151

[56] References Cited

U.S. PATENT DOCUMENTS

| | | | |
|---|---|---|---|
| 1,299,075 | 4/1919 | Wasylowich | 55/DIG. 33 |
| 3,105,617 | 10/1963 | Felldin | 55/361 |
| 3,240,567 | 3/1966 | Caparreli et al. | 55/361 |
| 3,548,823 | 12/1970 | Bogacik | 55/DIG. 35 |
| 3,665,681 | 5/1972 | Vitenko . | |
| 3,678,662 | 7/1972 | Grote . | |
| 3,779,909 | 12/1973 | Wisfeld et al. . | |
| 3,853,504 | 12/1974 | Buscher et al. . | |
| 4,116,649 | 9/1978 | Cullen et al. . | |
| 4,367,079 | 1/1983 | Wallsten | 55/387 |
| 4,401,447 | 8/1983 | Huber . | |
| 4,419,110 | 12/1983 | Ansite et al. . | |
| 4,449,646 | 5/1984 | Bonerb et al. . | |
| 4,502,876 | 5/1985 | Behnke, Jr. et al. . | |
| 4,683,065 | 7/1987 | Sheikh . | |
| 4,764,190 | 8/1988 | Israelson et al. . | |
| 4,818,122 | 4/1989 | Arbuthnot | 55/DIG. 33 |
| 4,925,465 | 5/1990 | Liskey . | |
| 4,986,912 | 1/1991 | Fisch . | |
| 5,017,287 | 5/1991 | Kuntz et al. . | |
| 5,022,902 | 6/1991 | Juhl et al. . | |
| 5,074,851 | 12/1991 | Plass et al. | 55/387 |

FOREIGN PATENT DOCUMENTS 869031 10/1941 France .

OTHER PUBLICATIONS

The Universal and the Fireman's Gas Mask, Dept of Interior, Technical paper 300, 1923, pp. 1 and 3.

*Primary Examiner*—Robert A. Dawson
*Assistant Examiner*—W. L. Walker
*Attorney, Agent, or Firm*—Cindrich & Titus

[57] ABSTRACT

The present invention relates to a lightweight and durable flexible-walled adsorber vessel that may be a free-standing unit, may be hung from an overhead support frame or ceiling, may float or be submersed in a body of liquid, or otherwise be suspended during use. The flexible adsorber of the present invention utilizes an internal screen, mesh, pallet or similar means to support carbon or other porous filter media so as to permit the pressurized or unpressurized removal of undesirable vapors, liquids or solids that may be present in streams of gas or liquid. Embodiments of the flexible adsorber are capable of supporting filter media weighing a ton or more, can resist deterioration in the presence of a variety toxic chemicals and/or corrosive agents, and can serve as a shipping container before or after use.

22 Claims, 18 Drawing Sheets

FLEXIBLE-WALLED ABSORBER

FIELD OF THE INVENTION

The present invention relates to a flexible-walled adsorber vessel that may be a freestanding unit or may be hung from an overhead support frame or ceiling. The flexible adsorber of the present invention utilizes an internal screen, mesh, pallet or similar means to support carbon or other porous filter media so as to permit the pressurized removal of undesirable vapors, liquids or solids that may be present in streams of gas or liquid. Embodiments of the flexible adsorber are capable of supporting filter media weighing a ton or more, can resist deterioration in the presence of heat and a variety toxic agents and corrosive chemical agents, and can serve as a shipping container before or after use.

BACKGROUND OF THE INVENTION

Rigid adsorption vessels are well known as devices for filtering vapors, liquids and solids from streams of gas or liquids. Typical filter canisters/adsorbers utilize inflexible metal or plastic walls to contain the filter media.

Solid-walled adsorption vessels devices are generally quite heavy, require the use of expensive materials, and are expensive to manufacture and maintain. Despite the thickness of the walls of such devices, even metals such as stainless steel will corrode in the presence of many chemicals, rapidly destroying the device.

U.S. Pat. No. 4,419,110 teaches a gas filter container for housing a filter capable of filtering gases containing toxic components, which "includes a flexible end wall adapted to be positioned against the body of the user and is secured by means of a series of straps . . . ." The flexible end wall of this small device includes inwardly-directed projections to space the wall from the filter inlet when the wall is deflected, so as maintain a communication path to the filter inlet.

U.S. Pat. No. 4,986,912 teaches "[a] disposable filter bag insert for use in a filter flexible adsorber assembly that comprises a rigid ring of diameter to overlie a shoulder on the flexible adsorber and be sealingly captured between the flexible adsorber base and top."

U.S. Pat. No. 4,925,465 teaches a vapor recovery flexible adsorber comprising a flexible envelope defining a chamber which contains an insulating material impregnated with hydrocarbon adsorbent. Preferably, the envelope includes a plurality of openings extending through the body of the flexible adsorber and sealed by sealing grommets to form mounting apertures adapted to receive a snap fit fastener attached to a body panel of a motor vehicle.

U.S. Pat. No. 5,022,902 discloses an absorbent package that resistants high temperature, comprises a bag that contains adsorbent, and a foil wrapping that is disposed about a portion of the bag, with the foil wrapping disposed adjacent to the bag.

U.S. Pat. No. 3,678,662 discloses a filter system to absorb and separate water and oil vapors from gases comprising a cylindrical container connectable in a supply line for said gases and containing at least one filter unit comprising a seamless cylindrical sleeve formed from textile material.

U.S. Pat. No. 4,401,447 discloses an adsorbent bag unit for installation in a refrigerant receiver.

U.S. Pat. No. 4,116,649 discloses an adsorbent unit including a container with an adsorbent bag, attached with a flexible flap to the container.

U.S. Pat. No. 4,502,876 discloses a cartridge for use in a rebreathing apparatus comprising a filtering device for removing carbon dioxide, a pair of flexible containers (one disposed within the other and in fluid communication with each other through a restricted opening), and among other features, a coaxial connector for fluidly connecting the cartridge to a rebreathing apparatus.

U.S. Pat. No. 3,853,504 discloses an apparatus and method for continuously precipitating liquid metals from gases, including sodium from protective gas of sodium cooled nuclear power plants that uses disc filters.

U.S. Pat. No. 3,665,681 discloses a smoke cleaning apparatus cleaning smoke particles from smoke which includes a mesh basket supported by a metal container.

French Patent No. 869,031 discloses a mesh filter material container.

The adsorber of the present invention can be suspended below the frame or ceiling via straps, wire, chain, or other means.

It would therefore be desirable to develop a flexible walled filter flexible adsorber that hangs from a frame or ceiling or that can be placed on a surface that will overcome the shortcomings of other flexible adsorbers.

SUMMARY OF THE INVENTION

The flexible adsorber of one embodiment of the present invention remains fixed by supporting straps and/or frame that adjacent to the upper surface of the flexible adsorber; further, the structure of the frame and straps holds it firmly in place. The flexible adsorber is supported by and its weight is evenly distributed among the straps, hooks and/or loops. A second set of loops, straps or hooks can be used to hold the lower portion of the flexible adsorber open, so as to permit unrestricted flow of the liquid or gas therethrough.

Other desirable embodiments may be placed on a surface and utilize an internal or semi-internal filter pallet structure.

The flexible adsorber of the present invention may desirably be constructed of a variety of permeable, semi-permeable and impermeable materials including, but not limited to, flexible polymer-based sheet materials, polyethylene, nylon, polybutylene, polypropylene, polyvinyl chloride, polyester or neoprene, of sheet, film, mesh, screen, porous sheet or cast material, woven or coated fabric construction, of a thickness or of a combination of laminates or liners or of a denier, with body heat sealed, sewn or adhered to meet the desired performance requirements.

Some of the materials that may be used include ketone-based resins such as polyetherketone (PEK), polyetheretherketone (PEEK), and the Fluoroplastics. Polytetrafluoroethylene (PTFE) is a particularly desirable material. PTFE coated with teflon, which may include a fluoropolymer-coated fiberglass fabric "sandwiched" between two cast fluoropolymer films is a particularly desirable construction. These materials offer extended service life, greater than or equal to prior stainless steel or other adsorber vessels. Virtually inert to all solvents and chemicals. Unique, cast-film technology provides the lowest possible permeation rate of any PTFE construction. Modified film surface for ease of fabrication.

Composite materials have been developed to combine the physical properties of our PTFE (Teflon®) coated fabrics with the vapor barrier properties of our PTFE cast films. This design allows for superior performance in chemically aggressive environments over a broad range of temperature (−400° F. to +500° F.) where vapor barrier properties are critical. Generally these materials include a backbone of fluoropolymer-coated fiberglass fabric "sandwiched" between two high-performance cast fluoropolymer films. Flexible adsorbers may also be internally supported using framework, support rods, or laminated ribs. Multiple layers of filter media or adsorbents may also be employed.

Desirable composite materials offer the following important benefits:
  Longer life over PTFE coated fabrics.
  Virtually inert to all solvents and chemicals.
  Cast-film technology provides the lowest possible permeation rate of any PTFE construction.
  Prepared film surface for ease of fabrication.
  Semi-conductive to dissipate static charge and prevent explosion hazards.
  High strength and durable, yet low weight for ease in handling and installation.
  Fiberglass reinforcement for added strength with maintained flexibility.
  Film surfaces provide better release properties (non-stick) than coated fabrics.

A number of structural properties are important to the performance of the flexible adsorber to include: material weight ($oz/yd^2$); thickness (mils); tensile PLI (lb/in); trap tear (lbs/ft.); permeation ($oz/ft^2/day$); and conductivity ($\Omega$/square).

Flexible adsorbers may also be equipped with attached ropes, webbed straps, or sleeves to provide loops for use as sling lifting devices to facilitate handling by mechanical equipment, ropes, straps or sleeves used for lifting must harness, encircle or be attached to the bag body. Flexible adsorbers may also be constructed with spouts for discharging purposes with top and bottom filling or discharging openings secured with coated wire ties or other means which will provide a gas and-/or liquid-tight closure.

Flexible adsorbers may be used to transport filter media before and after filtration, and subsequently refilled with fresh or reactivated filter media. The device should only be used to transport contaminated filter media when they are in such condition that they will protect the contents safely and efficiently.

Flexible adsorbers may be constructed without rigid bottoms but must be attached to a rigid pallet floor with two metal clamping rings. A pallet floor may be constructed of molded high density polyethylene designed with fork lift entry slots. Flexible adsorbers with an integral pallet base may be shipped without any lower movement protection.

A flexible adsorber filled with product or other material to simulate actual net weight to be contained should be capable of withstanding without damage or loss of product a free drop of two feet onto a solid concrete surface.

Desirably, for larger-sized embodiments of the present invention, support straps, slings and harnesses, as well as the adsorber itself, should be capable of providing a 2:1 safety factor tested by simulating a load of two times the actual weight apportioned each loop used for lifting purposes without failure. For example, if the total net weight of container is equal to 1,000 pounds and the container is outfitted with four loops for vertical lifting purposes, each loop must be capable of lifting a weight of 500 pounds. Testing may be accomplished by filling the container to a weight of 1,000 pounds and lifting by use of two opposing loops or by filling the container to a weight of 2,000 pounds and lifting by use of all four loops. A flexible adsorber of the present invention may be able to support adsorbent (and trapped contaminates) weighing a ton or more, yet the vessel itself may weigh under fifty pounds.

Certain embodiments of the present invention may include a mesh inner floor, and a lower chamber that "inflates" to insure even (upward, downward or lateral) fluid flow. The device could also be used for liquids, and can readily be suspended from floats in a body of water for water purification/decontamination procedures.

The present invention meets industrial needs for cost-effective removal of gas and liquid-borne contaminants, to include volatile organic compounds (VOCs) at air emission sources. The adsorber can handle air flows of 1,000 cfm and more.

The present invention may be used to remove both toxic and non-toxic contaminants, and is especially useful for short-term projects and for treatment of low volume flows that contain low to moderate VOC concentrations. Common applications include VOC removal from process vents, soil remediation vents, and air stripper off-gases. When carbon becomes saturated with VOCs, the system is replaced with another adsorber containing fresh carbon. To accommodate a wide variety of process conditions, the flexible adsorbers of the present invention withstand elevated temperatures and pressure or vacuum conditions.

Users of the flexible adsorber can generally achieve contaminant removal and regulatory compliance objectives, minimize operating costs, and eliminate maintenance costs. Furthermore, because organic compounds are safely destroyed through the carbon reactivation process, costs and regulations typically associated with waste disposal can be eliminated. The flexible adsorber is specifically designed for ease of shipment, installation and operation. System can be operated in series or parallel mode or a combination of both modes to handle a variety of flows and concentrations.

Performance trials were conducted to determine the feasibility and performance of the flexible adsorber of the present invention. Leak tests were conducted using a soap solution to detect leaks under pressure and stress at all seams. Air flow and pressure drop measurements were measured at several carbon loading capacities. BPL 4×10 mesh carbon was selected for these trials; pelletized and other carbons and various porous filter media will perform much like the mesh carbons tested.

Embodiments of the flexible adsorber unit were "hang" loaded with up to 1000 pounds and more of BPL mesh 4×10 of carbon over time to observe and measure physical stretching and stress performance of the fabric. The flexible adsorber was suspended in an frame. One embodiment was equipped with six hanging straps attached to the upper portion of two opposing side walls. Air flow was supplied from the fan used to test the upper and lower exhaust/intakes of the adsorber. The adsorber was pressurized with an NYB model 2108A fan with 1000 cfm capacity @36 in. w.g., 3500 rpm, controlled with a vane type damper on the fan inlet. Fan discharge to the flexible adsorber bottom inlet spout was accomplished with 8" diameter thin wall flexible duct. Flow and pressure drop was measured in inches of water using a stationary vertical manometer connected to a pitot tube station with air straightener-equalizer.

Flow versus pressure drop measurements were made with the unit empty and loaded with 600, 800, 1000 lbs. of BPL 4×10 carbon. Results of these pressure drop tests are set forth in Table I.

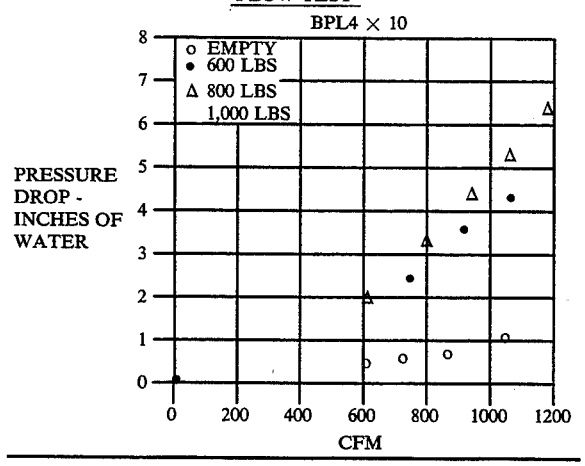

TABLE I — FLOW TEST — BPL4 × 10

Leak testing was performed by introducing air flow into the bottom spout, and restricting the top exit port so as to create internal back pressure. Soap solution applied to all seams indicated leaks at seam intersections of an early embodiment (outside corner material fold) of the inlet spout and bottom skirt.

The loaded unit (as shown in FIGS. 1, 2 and 3) hang "fits" within a square frame; other embodiments may fit in a cylindrical frame, or an overhead rack without sides. It may be desirable in some embodiments to prevent the side walls and side straps from contacting the frame side braces. In some embodiments, the walls may tend to sag or collapse so as to prevent uniform contact of the intake vapor with the filter media support screen. Placement of the screen floor (filter media bed support) approximately five inches up the side wall from the bottom skirt seems to work well, allowing air flow to inflate this area. The screen floor sags but doesn't block the inlet spout. In some square embodiments, the corners and/or side walls may tend to sag or collapse against the frame; the use of internal support hoops and external loops and/or straps can prevent this effect.

After flow tests were completed the flexible adsorber and frame were transported with the fork truck over rough ground with the intent of settling the carbon. In one embodiment, failure of the fabric occurred. The material separated in an even line just below the point of attachment of the straps.

Another embodiment was made that included adding a strap to each side, in an arrangement of three straps per side as shown in FIG. 3. The straps of this embodiment were extended to terminate at the screen floor area. The maximum fill for a medium-sized unit (prior to exposure to the steam to be filtered) is recommended to be 800 pounds, although similar embodiments can undoubtedly hold far greater loads.

Embodiments of the present invention are also such that the flexible adsorber can be suspended from a ceiling, boom, floats or otherwise as to permit adsorption by the filter media.

Other details, objects and advantages of the flexible adsorber will become more readily apparent from the following descriptions of the presently preferred embodiments thereof.

BRIEF DESCRIPTION OF THE DRAWINGS

In the accompanying drawings, preferred embodiments of the invention are illustrated by way of example only, wherein.

DESCRIPTION OF THE PREFERRED EMBODIMENTS

Figure 1:
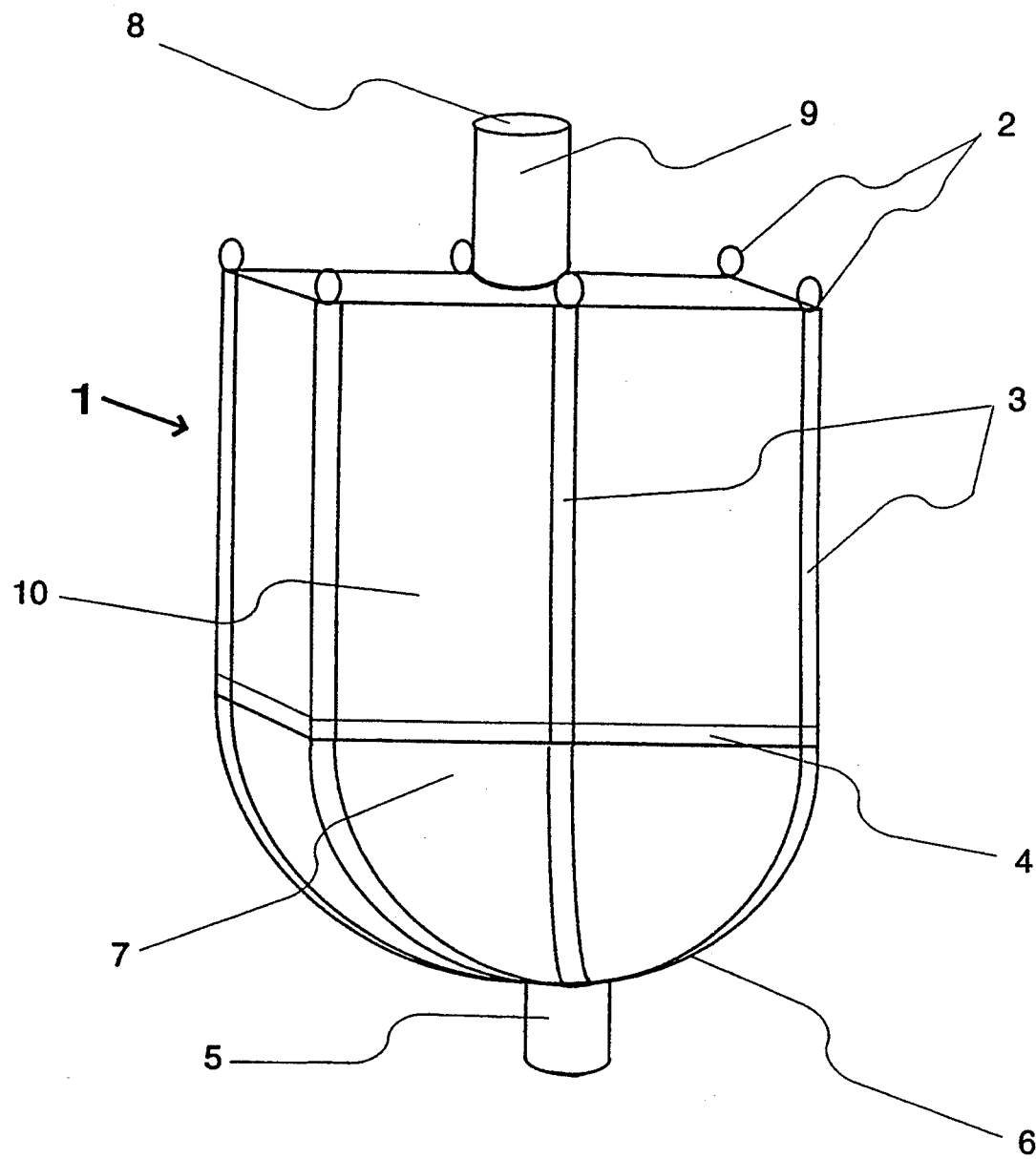
FIG. 1 shows a perspective view of the flexible adsorber of the present invention.

FIG. 1 shows flexible adsorber 1 capable of being suspended from loops 2 of straps 3 at six points on the device. Loops 4 are used to hold the bottom portion of the bag open so as to permit unrestricted of vapors from the bottom of adsorber 1. Intake port 5 at the bottom of adsorber 1 permits the vapors to be purified to enter the adsorber, wherein they pass through a screen into the adsorption bed (inside flexible adsorber 1 and not shown in FIG. 1). A "support pallet" as shown in FIGS. 5 through 8 that follow may also be employed to support the adsorbent inside the flexible adsorber shown in FIG. A variety of adsorbents (including carbons) can be utilized in the adsorption bed; desirable embodiments of the present invention may utilize pelletized carbons, of a mesh size larger than the mesh size of the internal screen, to prevent that adsorbent from falling through the internal screen onto the into bottom portion 6 of flexible adsorber 1. Desirably, the entire screen is exposed to the lower chamber 7 of adsorber 1, so that the entire lower surface of the adsorption bed is utilized. The adsorbent contained in zone 10 holds the outer wall of flexible adsorber 1 open, so that no supports need be used to maintain the adsorption bed in position for use. As the vapors enter intake port 5 (or exit port 8) of the flexible adsorber, they are forced via pressure up through (or down through) the adsorption bed, and exit the opposite port.

Straps 3 of flexible adsorber 1 run the entire length of the sides of the adsorber. The straps are intended to ensure that the weight of the adsorption bed inside flexible adsorber 1 are supported from the bottom portion of the bed adjacent to the internal screen. In this sense the straps are intended to directly support screen 6, which holds most of the weight of the adsorption bed.

Figure 2:
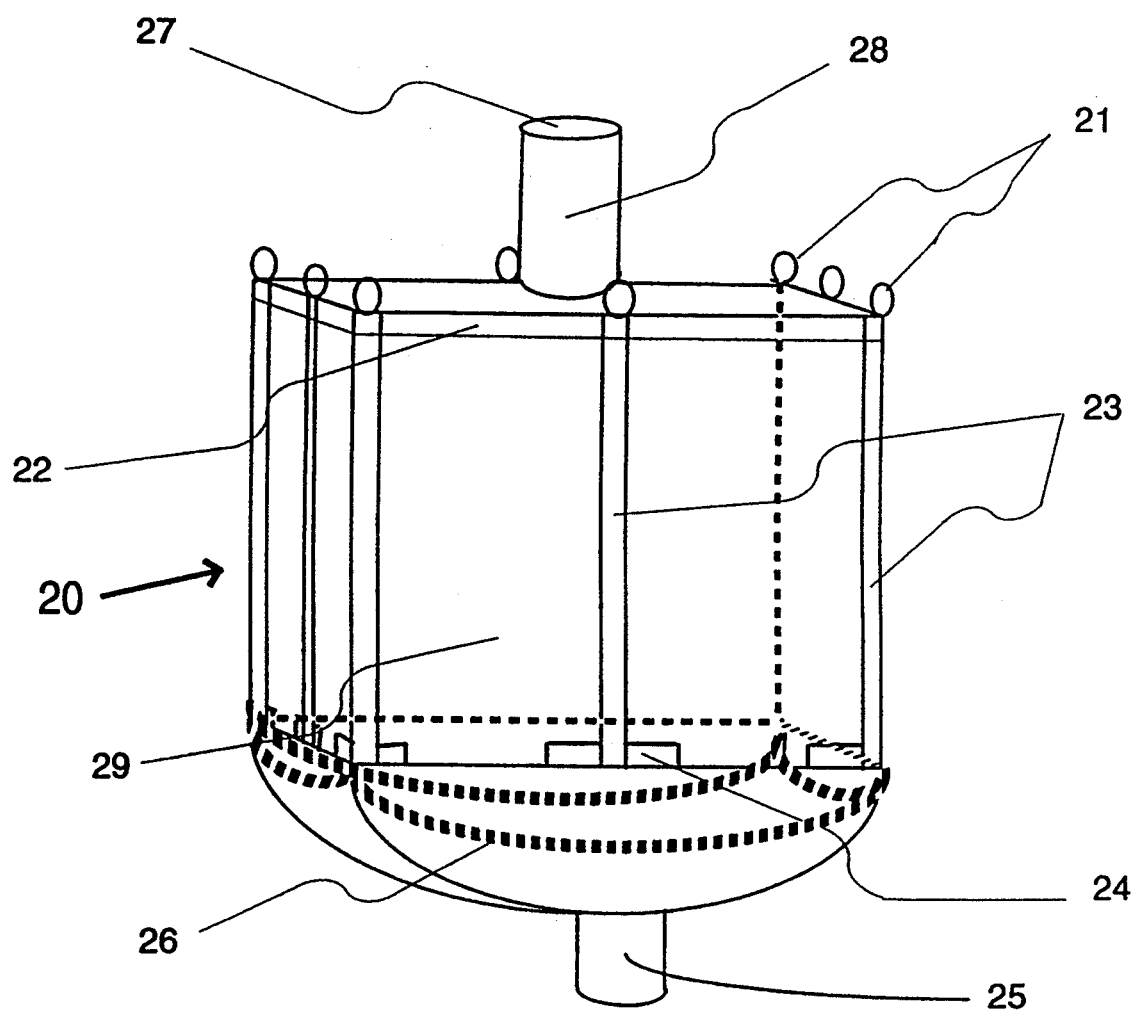
FIG. 2 shows a perspective view of the flexible adsorber of the present invention.

FIG. 2 shows another embodiment of flexible adsorber 20, which is equipped with eight strap loops 21 at the upper corners of the adsorber; upper strap 22 connects straps 23, while lower strap tabs 24 help reinforce the attachment of straps 21 to the sides of flexible adsorber 20. Flexible adsorber 20 as shown in FIG. 2 shows intake port 25 receiving contaminated vapors or liquids, which pass through a screen flooring 26, (the outline of which is shown in cutaway) into the adsorption bed purified gases are thereafter vented from the adsorber from port 27 of exhaust 28. The direction of flow may be reversed with contaminated vapors or liquids entering port 27, passing through the adsorption bed, and then exiting from port 25. Again, the adsorbent contained in zone 29 holds the outer wall of flexible adsorber 1 open, so that no supports need be used to maintain the adsorption bed in position for use.

Figure 3:
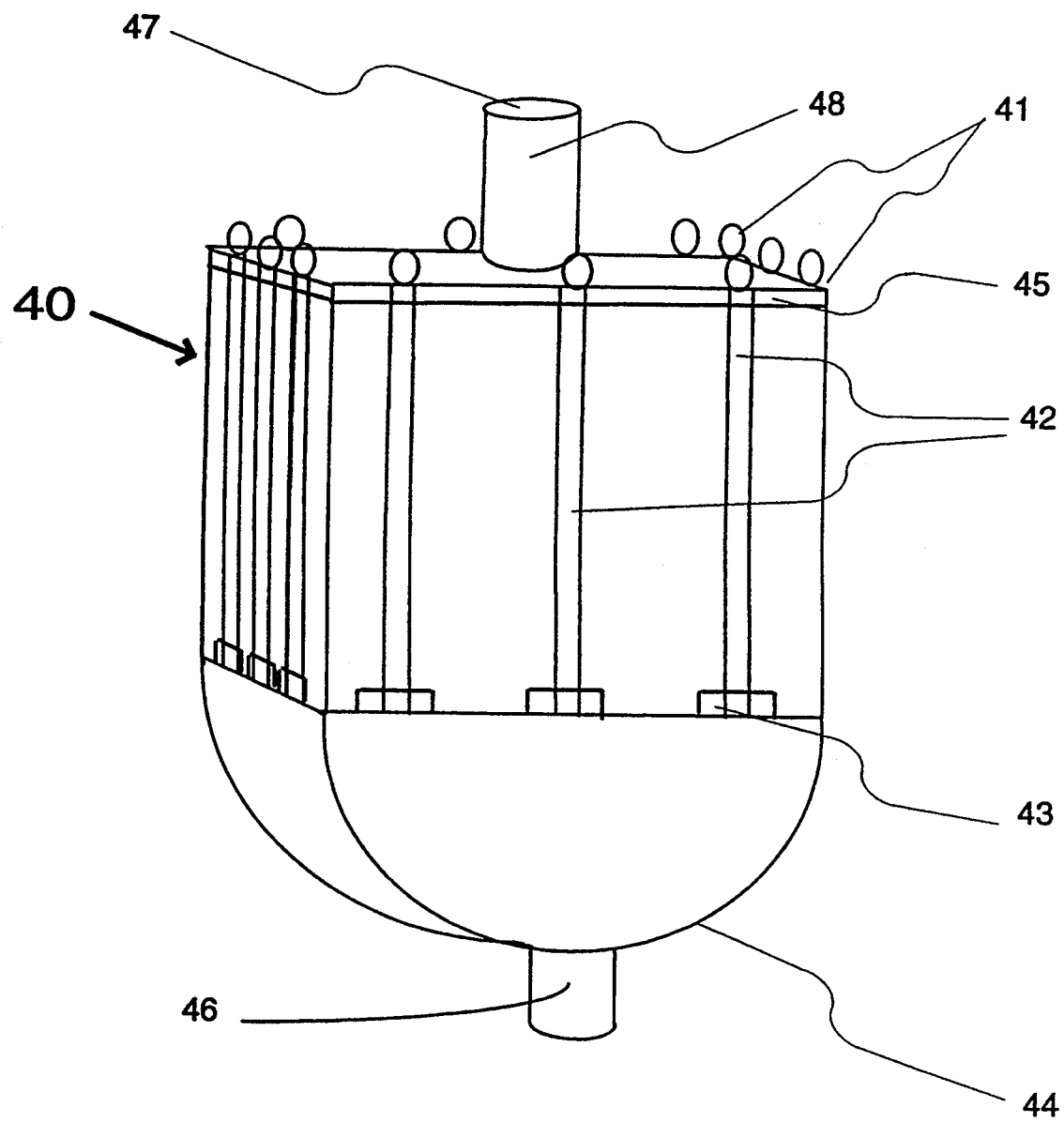
FIG. 3 shows a perspective view of the flexible adsorber of the present invention.

FIG. 3 shows flexible adsorber 40 with a more extensive array of nine support straps. Flexible adsorber 40 as shown in FIG. 3 is suspended from a total of nine (9) loops 41; nine (9) straps 42 extend below loops 41, and disperse the load of the entire adsorber along the sides of the vessel. Nine (9) inverted "T" braces 43 are attached to the lower end of each of the six straps 42, and further disperse the load of the adsorber on each strap 42. The loops and straps on the flexible adsorber hold the bottom portion 44 of the device bag open so as to permit unrestricted flow of vapors up from (or down to) the bottom of adsorber 40. A continuous support strap 45 runs around the circumference of the upper portion of flexible adsorber 40, adding support to straps 42 below loops 41. Intake port 46 at the bottom of adsorber 40 permits the vapors to be purified to enter the adsorber; filtered vapors eventually exit port 47 of exhaust 48. The direction of flow for the vapors or liquids to be treated may also be reversed, as fluids may enter the device from either port 46 or port 47, then pass through the adsorbent bed and exit the opposite port. A reinforced flexible adsorber of the present invention may be able to hold adsorbent and trapped contaminates weighing a ton or more, yet the adsorber vessel itself may weigh under fifty pounds.

Figure 4A:
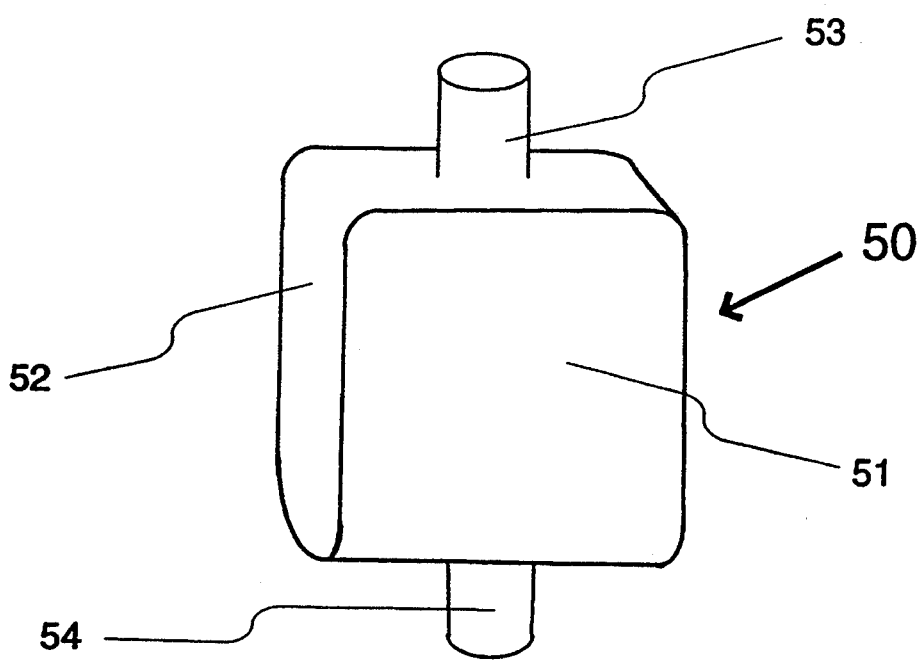
FIGS. 4A and 4B show an embodiment of the flexible adsorber of the present invention.

FIG. 4A shows flexible adsorber 50 that does not require support straps. The walls of flexible adsorber 50 may be formed from only two portions or pieces of flexible material 51 and 52, which may form the outer surfaces of the adsorber much like the cover surrounds the core of a baseball. Like the embodiments shown in FIGS. 1 and 2, an internal screen provides the support for the adsorbent inside, although a "support pallet" as shown in FIGS. 5 through 8 that follow may also be employed to support the adsorbent inside the flexible adsorber shown in FIG. 4A. Most suitable for lighter or smaller adsorbent loads, flexible adsorber 50 as shown in FIG. 4A may be attached to a treatment source from intake port 53 at the top of the adsorber, passed downward through the adsorber and out exhaust port 54.

Figure 4B:
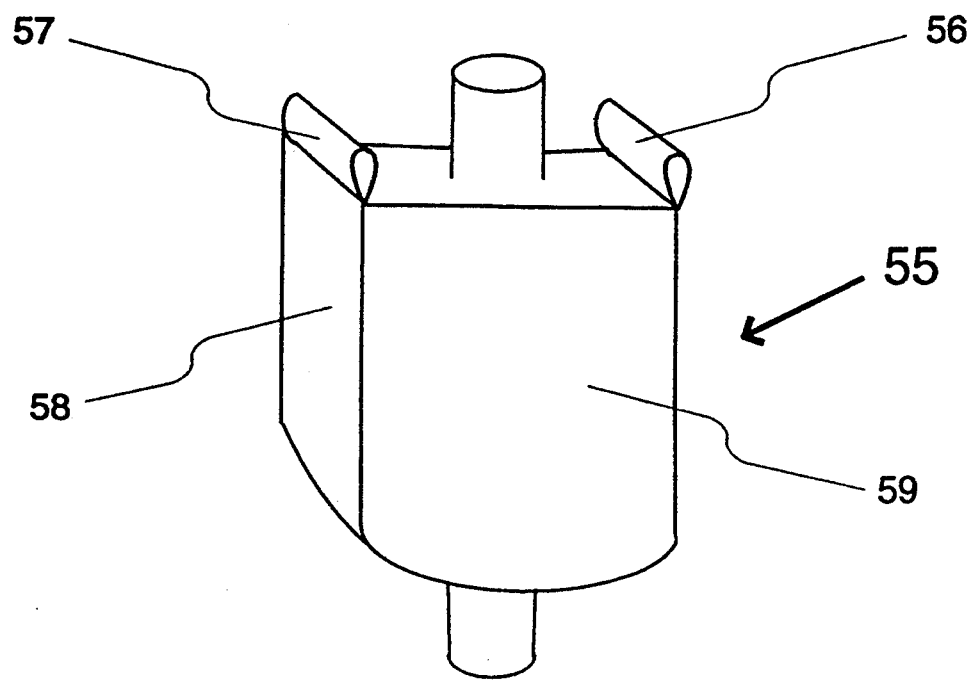

FIG. 4B shows flexible adsorber 55 that also does not require support straps. Wall section 58 of flexible adsorber 55 may be formed at each end into continuous straps 56 and 57 which may provide the means to hang the adsorber. The embodiment of the present invention shown in FIG. 4B may be suitable for light or heavy adsorbent loads, as the continuous straps 56 and 57 may effectively support the weight of the device, while greatly simplifying the construction of the device. Wall section 59 completes the exterior of the flexible adsorber 55; unfiltered vapors or liquids enter from the top or bottom port, and filtered vapors or liquids exit from the opposite port.

Figure 5:
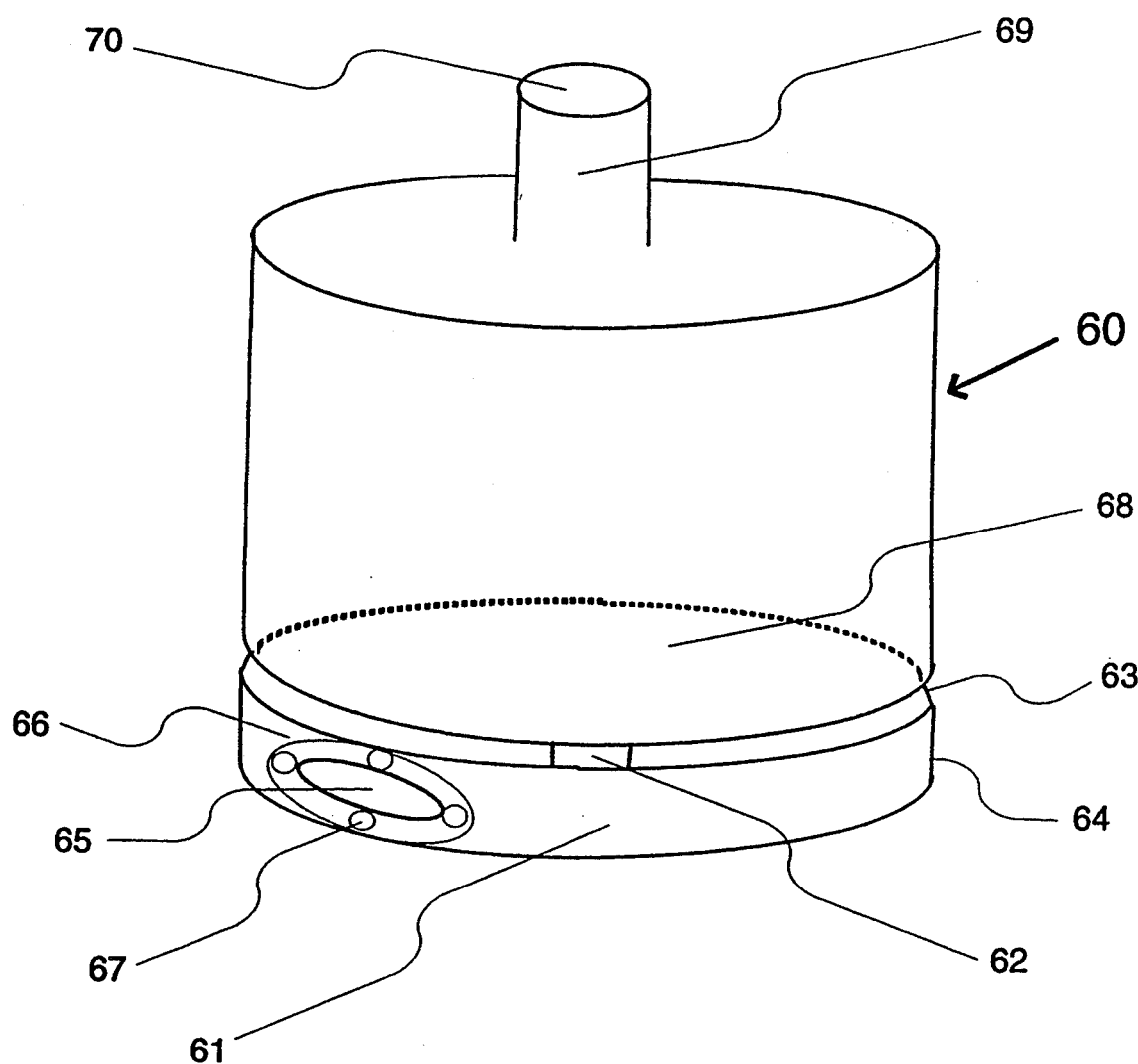
FIG. 5 shows a freestanding embodiment of the filter pallet of present invention.

FIG. 5 shows a "freestanding" flexible adsorber 60, that does not require suspension from an array of support straps or harnesses; rather, adsorber 60 rests on its own filter pallet 61, which may be sealed completely or partially inside flexible adsorber 60.

If filter pallet 61 is only partially inside flexible adsorber 60, retaining band 62 can be used to seal the lower edge of wall 63 of flexible adsorber 60 in retaining grove 64, formed along the upper edge of filter pallet 61. The source of the unpurified vapor or liquid may be sealingly connected to either port 65 or port 70. Port 65 requires fastening to flange 66, using clamps, pins, bolts, screws or similar fastening means through holes 67.

If a filter pallet is positioned entirely inside flexible adsorber 60, a retaining band is not required; rather, the filter pallet may merely rest on the lower floor of the flexible adsorber 60.

Figure 6:
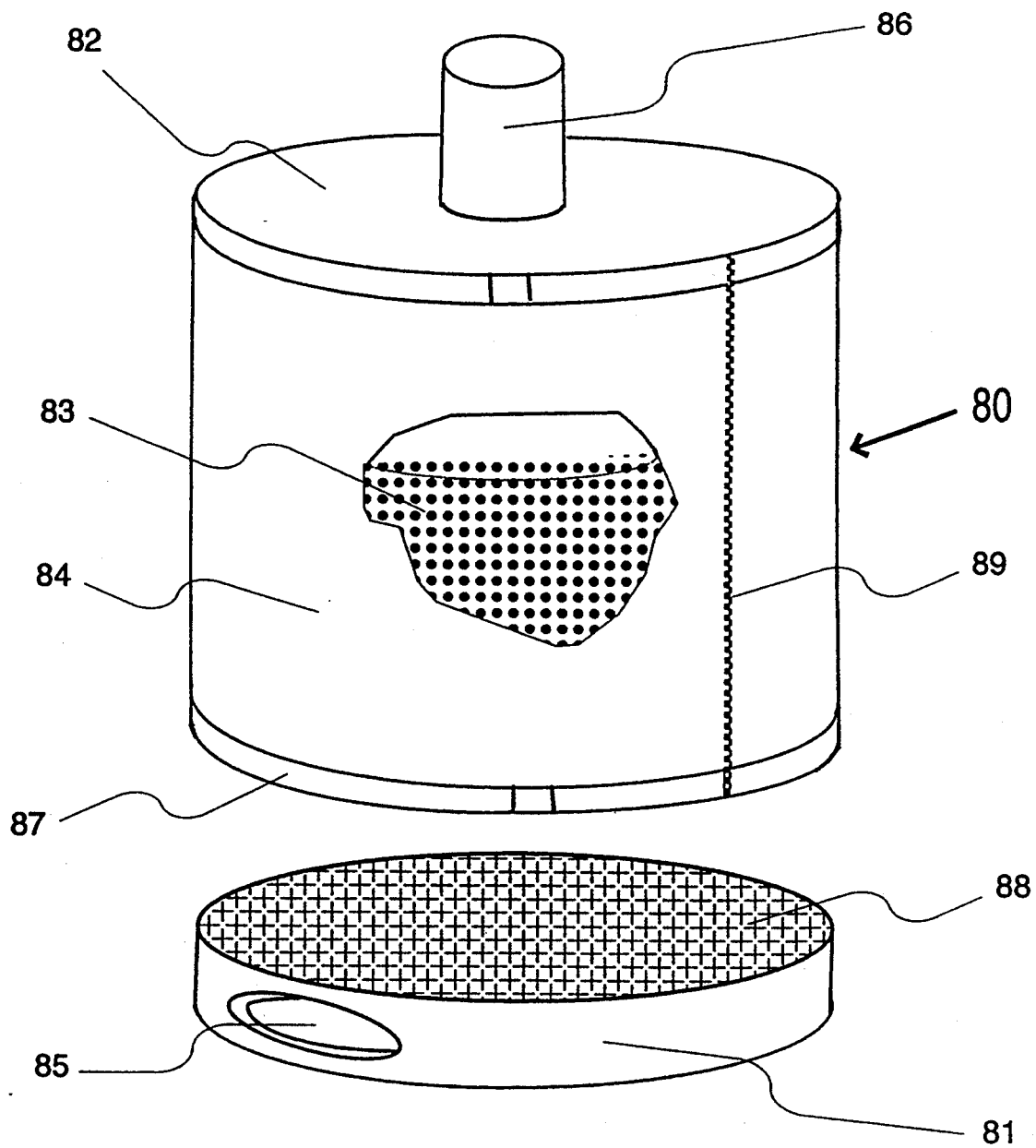
FIG. 6 shows another freestanding embodiment of the present invention.

FIG. 6 shows a "freestanding" flexible adsorber 80, that does not require suspension from an array of support straps or harnesses. Adsorber 80 rests on its own filter pallet 81 (shown disassembled from the adsorber), which may be sealed completely inside or partially inside flexible adsorber 80.

Rigid (or semirigid) upper cover 82 is continuously formed, heat sealed, glued, sewn, or otherwise attached to exhaust port 86. Upper cover 82 is likewise continuously clamped, formed, heat sealed, glued, sewn, or otherwise attached to the top edge of flexible adsorber 80. Filter media 83 is shown inside flexible adsorber 80 through the illustrated cutaway portion of wall 84. FIG. 6 also shows that side mount intake port 85 for unpurified vapor or liquid may be sealingly connected to an intake line using clamps, pins, bolts, screws or similar fastening means; exhaust port 86 for purified vapor may likewise be sealingly connected to an exhaust line, or to the atmosphere. The source of the unpurified vapor or liquid may be sealingly connected to either port 65 or port 70. Port 65 requires fastening to flange 66, using clamps, pins, bolts, screws or similar fastening means through holes 67. If filter pallet 81 is only partially inside flexible adsorber 80, retaining band 87 can be used to seal the lower edge of wall 84 of flexible adsorber 80; pallet screen 88 supports the filter media inside flexible adsorber 80. A single rectangular sheet of material may be used to form cylindrical wall 84, when opposite ends of the rectangular sheet are joined at seam 89.

Figure 7:
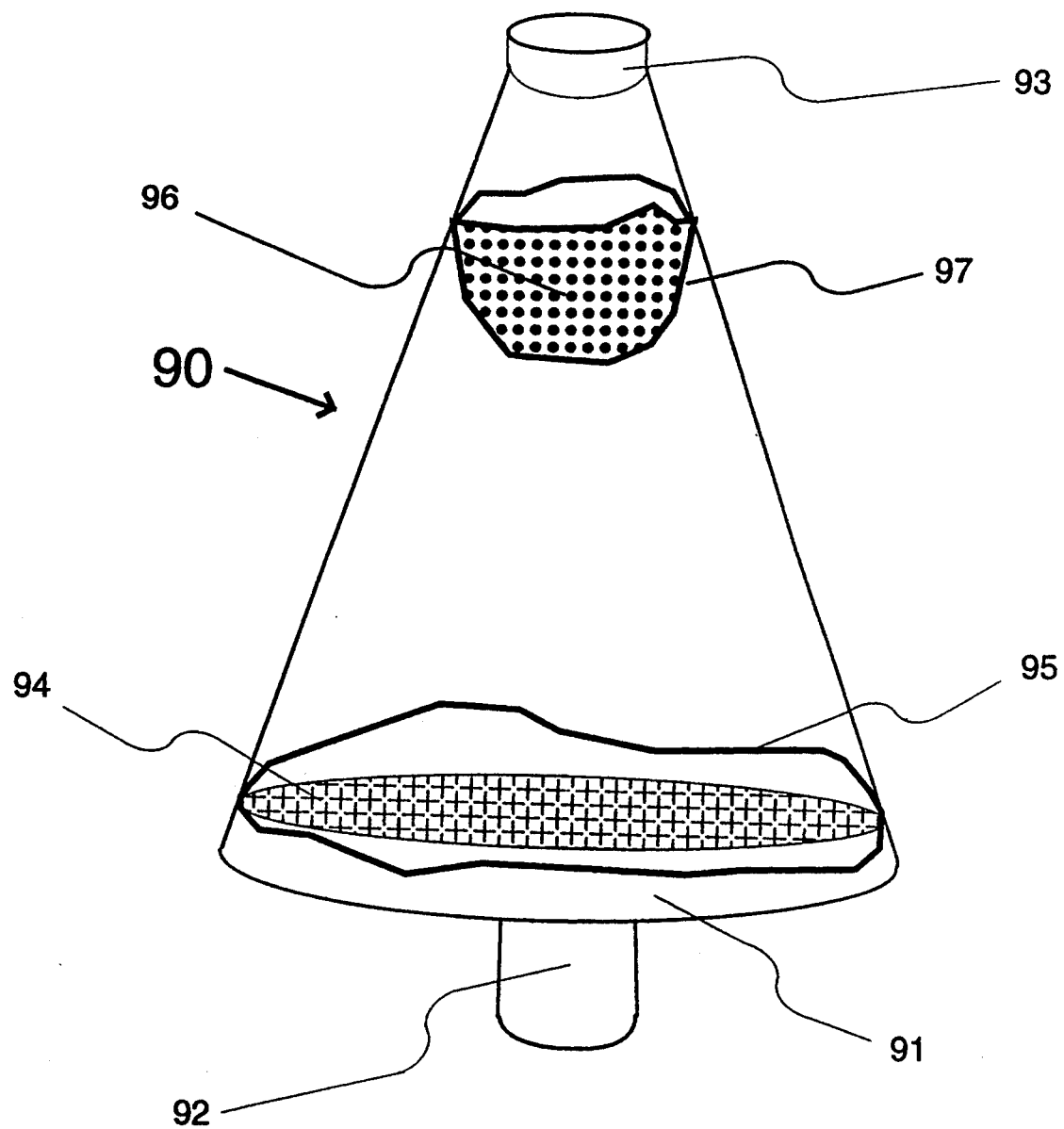
FIG. 7 shows a cone-shaped embodiment of the flexible adsorber of the present invention.

FIG. 7 shows a "freestanding" (or suspendable) cone-shaped flexible adsorber 90, with a circular filter pallet 91. Intake (or exhaust) port 92 for vapor or liquid may be sealingly connected to an external line using clamps, pins, bolts, screws or similar fastening means; exhaust (or intake) port 93 may likewise be sealingly connected to an external line. In the downflow mode of treatment, the filter media adsorbs contaminants from top to bottom. As the filter media adsorbs the desired materials from the stream of liquid or vapor flowing through the flexible adsorber, the cone shape of the embodiment shown in FIG. 7 places the greatest useful mass of the adsorbent in the wide portion of the cone, where the full adsorptive capacity of the adsorbent will first be utilized. Filter screen 94 (shown inside cutaway portion 95 of the adsorber) is capable of supporting the desired filter media 96 (shown in cutaway portion of 97 of flexible adsorber 90).

Figure 8:
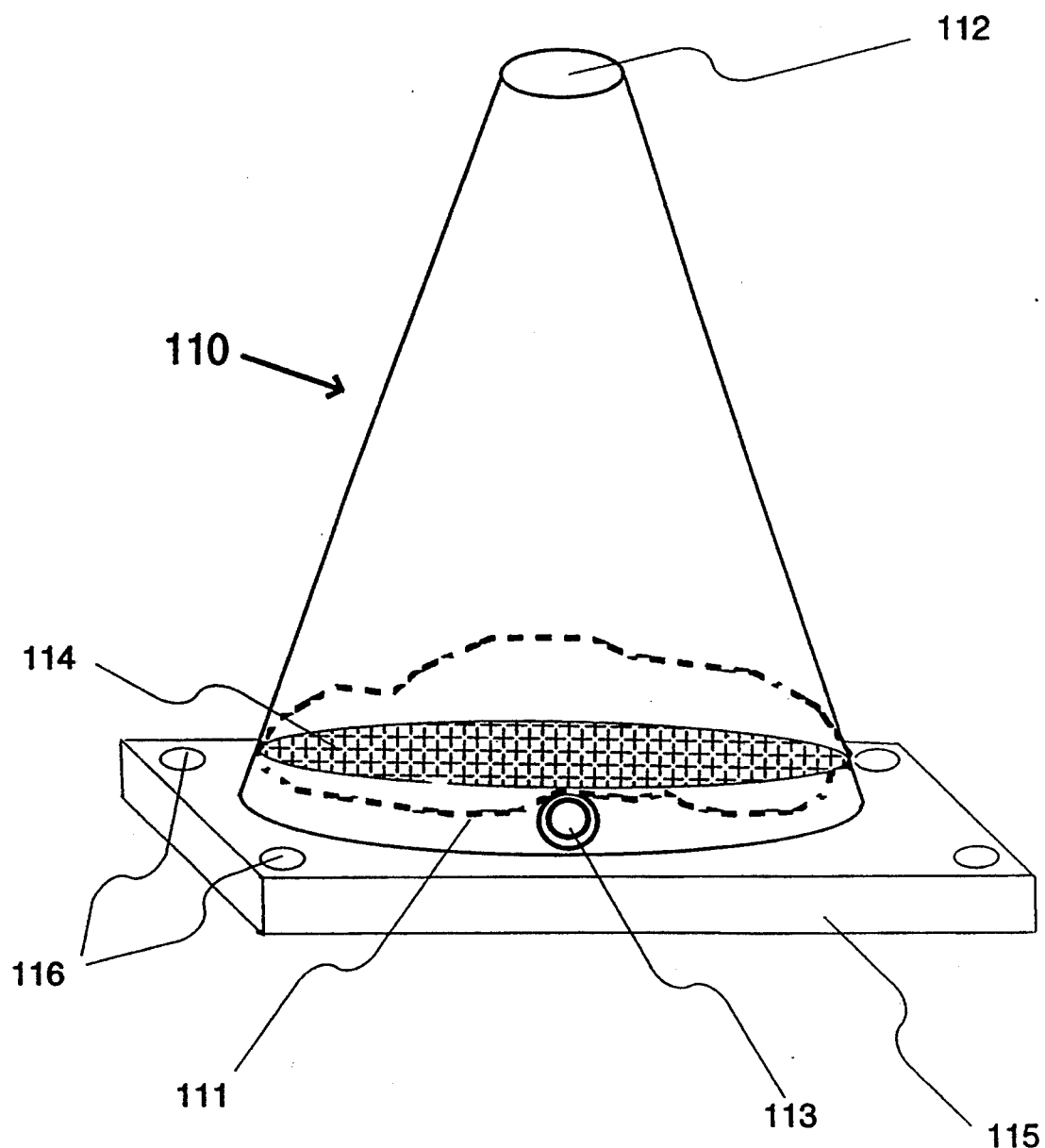
FIG. 8 shows another cone-shaped embodiment of a filter pallet of the present invention.

FIG. 8 shows a "freestanding" (or suspendable) cone-shaped flexible adsorber 110, with a circular filter pallet 111. Intake (or exhaust) port 112 for vapor or liquid may be sealingly connected to an external line using clamps, pins, bolts, screws or similar fastening means; exhaust (or intake) port 113 may likewise be sealingly connected to an external line. Filter screen 114 (shown inside the cutaway portion of the adsorber) is capable of supporting the desired filter media 96 (shown in cutaway portion of 97 of flexible adsorber 90).

Figure 9:
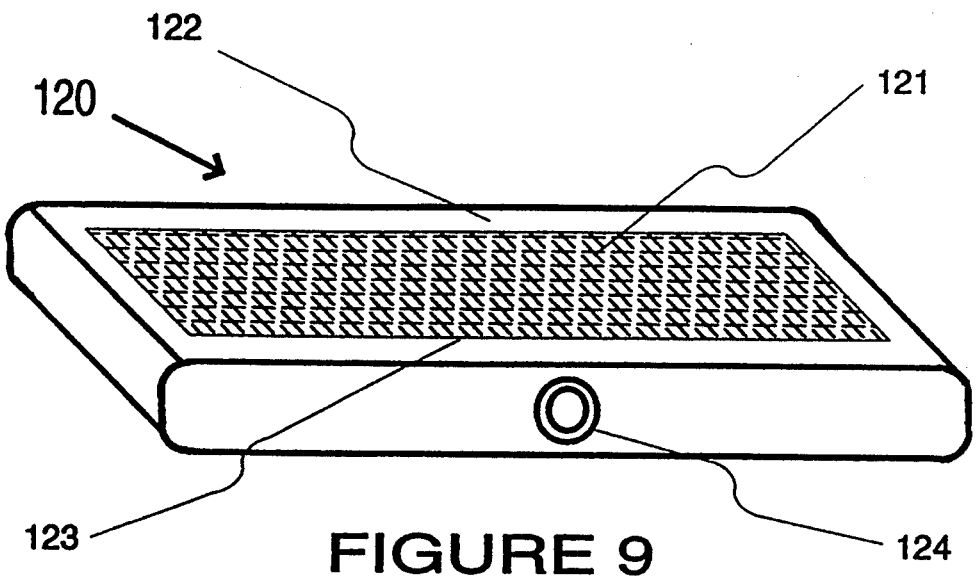
FIGS. 9, 10 and 11 show another embodiment of the filter pallet and screen of the present invention.
Figure 10:
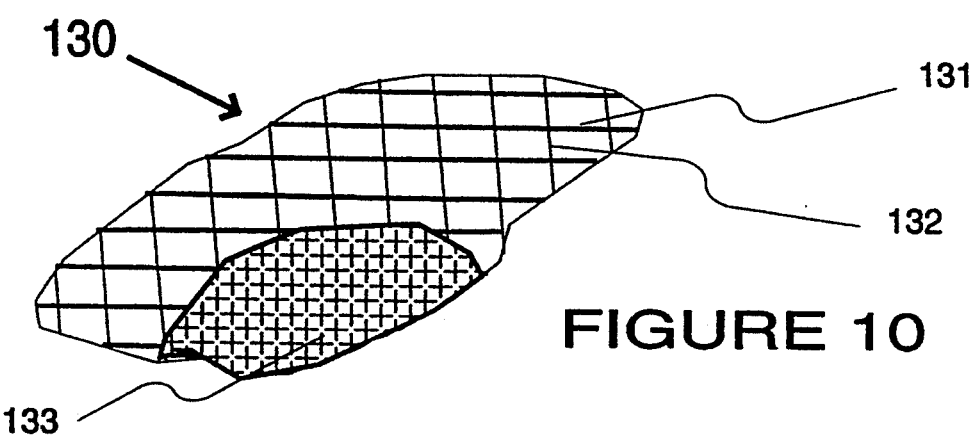
Figure 11:
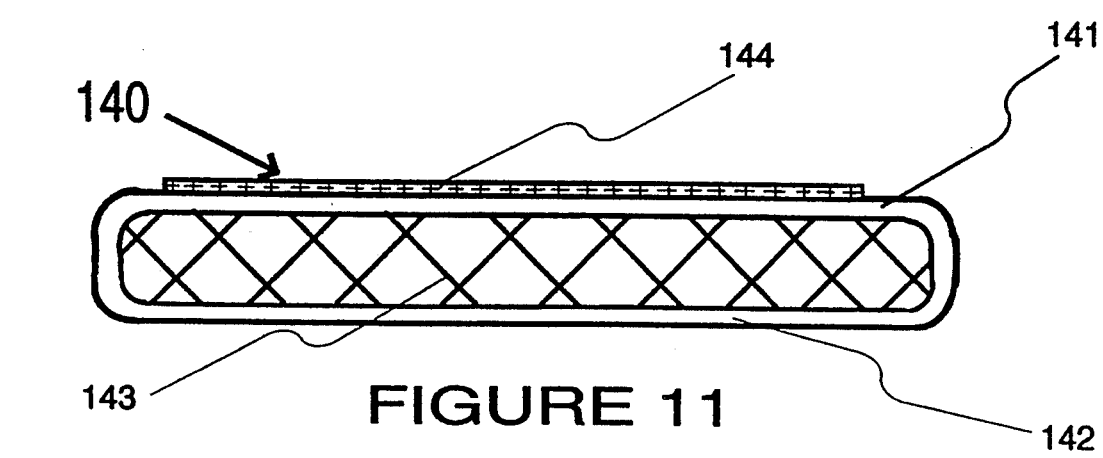

FIGS. 9, 10 and 11 show other embodiments of the screen and or screen pallets to be used in the flexible adsorbers of the present invention. FIG. 9 shows filter pallet 120 which may support the filter media in the hanging or suspended embodiments of the flexible adsorbers (to include those shown in FIGS. 1 through 4B), as well as in the surface mount versions of the present invention (including those shown in FIGS. 5 through 8). Upper screen 121 is mounted to the upper surface 122 of filter pallet 120, and is secured in place with retaining ring 123. The hollow interior of filter pallet 120 insures that the unpurified vapors entering through intake port 124 can be uniformly dispersed along upper screen 121, for eventual flow through adsorption by the filter media immediately above filter pallet 120. The source of the unpurified vapor may be sealingly connected to an intake line.

FIG. 10 shows a cutaway view of a reinforced screen 130, which may also be used in filter pallet 120 as shown in FIG. 10, or as shown in FIGS. 5 through 8; reinforced screen 130 may also be used in suspended versions of the present invention, including those shown in shown in FIGS. 1 through 4B. Screen 130 is comprised of a course support or reinforcing mesh, with support strands 131 woven over support strands 132 at right angles. A fine mesh 133 (shown in cutaway) overlies support strands 131 and 132, and provides the necessary barrier for the fines of the filter media that rest on the entire screen 130.

FIG. 11 shows a cutaway view of a filter pallet 140, such as may also be used in filter pallet 120 as shown in FIG. 10, or as shown in FIGS. 5 through 8; reinforced screen 130 may also be used in suspended versions of the present invention, including those shown in shown in FIGS. 1 through 4B. Upper pallet layer 141 is held above lower pallet layer 142 by support layer 143, a lightweight yet sturdy honeycomb or similar structural system capable of permitting liquid and/or vapor to circulate between layers 141 and 142. A screen 144 may be placed over the upper layer 141, unless the honeycomb formation of support layer 143 is so fine or dense in comparison to the filter media that no screen 144 is required.

Figure 12:
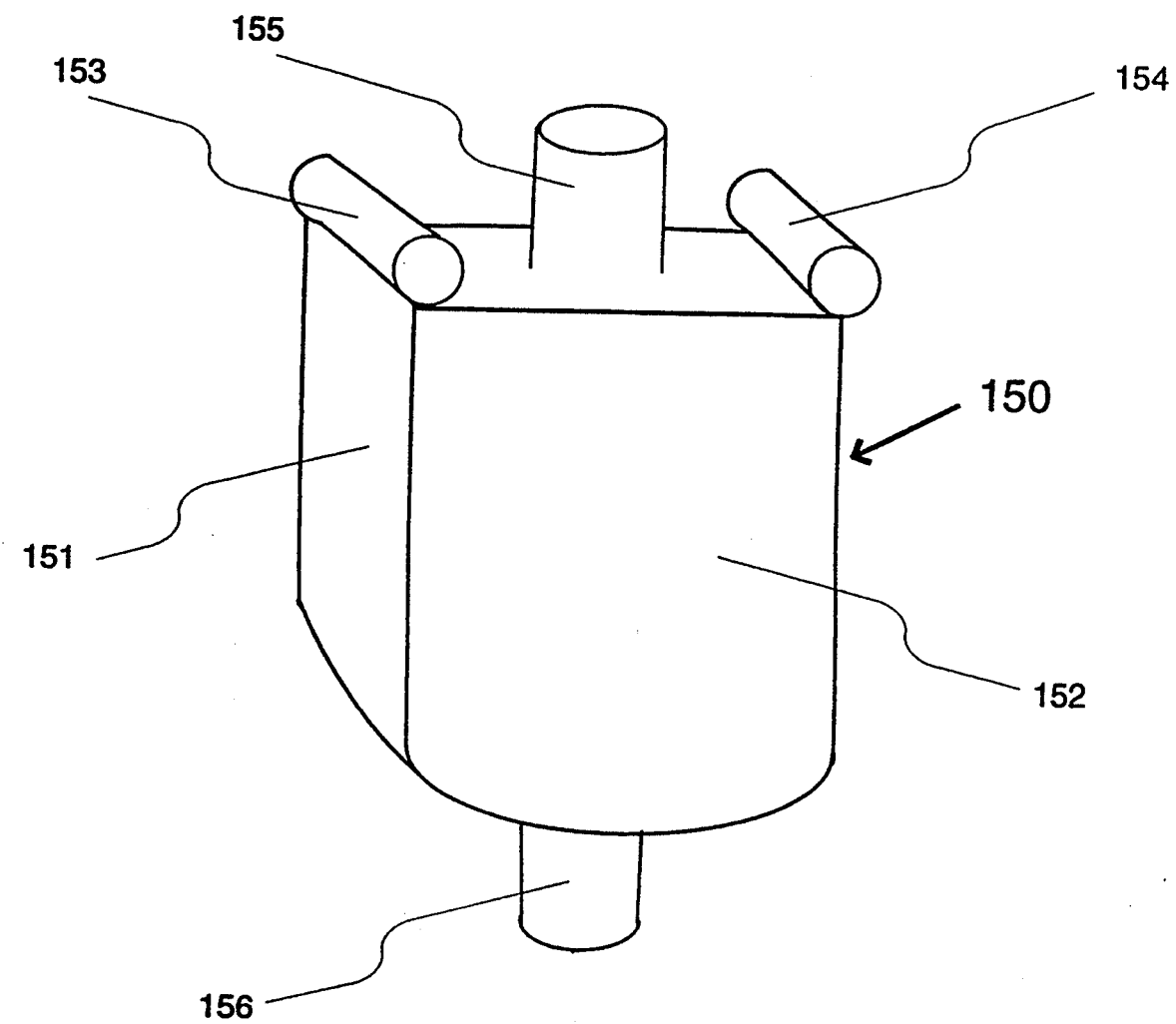
FIG. 12 shows a floating embodiment of the flexible adsorber of the present invention.

FIG. 12 shows a floating flexible adsorber 150, the external surface capable of being formed from two lengths of flexible material, rectangular portion 151 and rectangular portion 152. Flexible adsorber 150 may be suspended from floats 153 and 154 in a body of water.

A single continuous seam connects rectangular portion 151 to rectangular portion 152, much the way two pieces of leather form the cover on a baseball. The corners of rectangular portions 151 and 152 may preferably be rounded so as to permit a more secure seal, and to avoid sharp corners that can contribute to leakage of the liquid (or vapors related to those liquids) from the interior of the device. The source of the unpurified liquid may be sealingly connected to intake port 156 by adhesive, clamps, pins, bolts, screws or similar fastening means; purified liquid may be expelled via exhaust port 155, connected to an exhaust line adhesive, clamps, pins, bolts, screws or similar fastening means. The direction of the flow of liquid in flexible adsorber 150 may, like other embodiments, be from top to bottom, or side to side if floats 153 and 154 are positioned at other locations on flexible adsorber 150.

Figure 13:
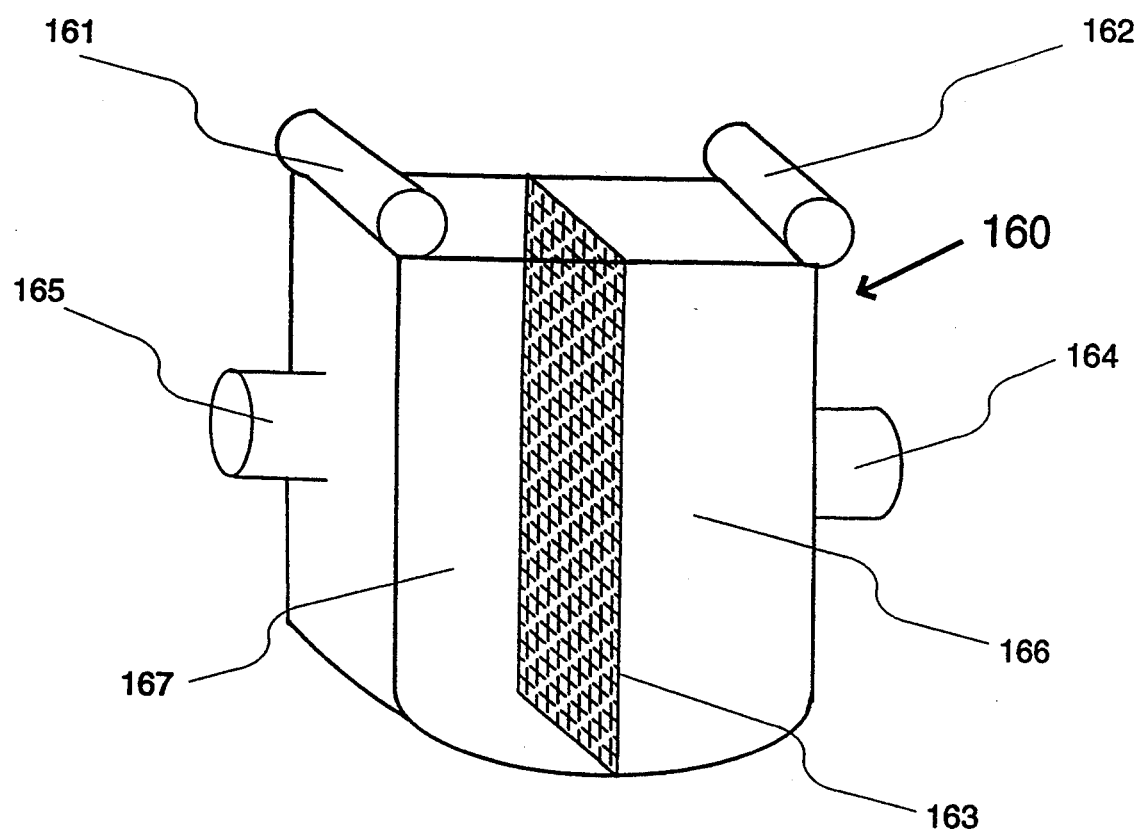
FIG. 13 shows another floating embodiment of the flexible adsorber of the present invention.

FIG. 13 shows a floating flexible adsorber 160, which may be suspended from floats 161 and 162 in a body of water. The flexible adsorber of this embodiment may also be configured with an internal vertical pallet (or screen) 163, as that pallet is shown in FIGS. 1 through 4B and 9 through 11. The source of the unpurified may be sealingly connected to side intake port 164 by adhesive, clamps, pins, bolts, screws or similar fastening means; purified liquid may be expelled via side exhaust port 165, connected to an exhaust line adhesive, clamps, pins, bolts, screws or similar fastening means. Chamber 166 may hold the adsorbent, while chamber 167 holds the purified effluent prior to discharge from the exhaust port 165. An integral or attached pump may be used to force fluid through the flexible adsorbers shown in FIGS. 12 and 13, as well as the flexible adsorbers shown in FIGS. 1 through 8 and 16 through 20.

Figure 14:
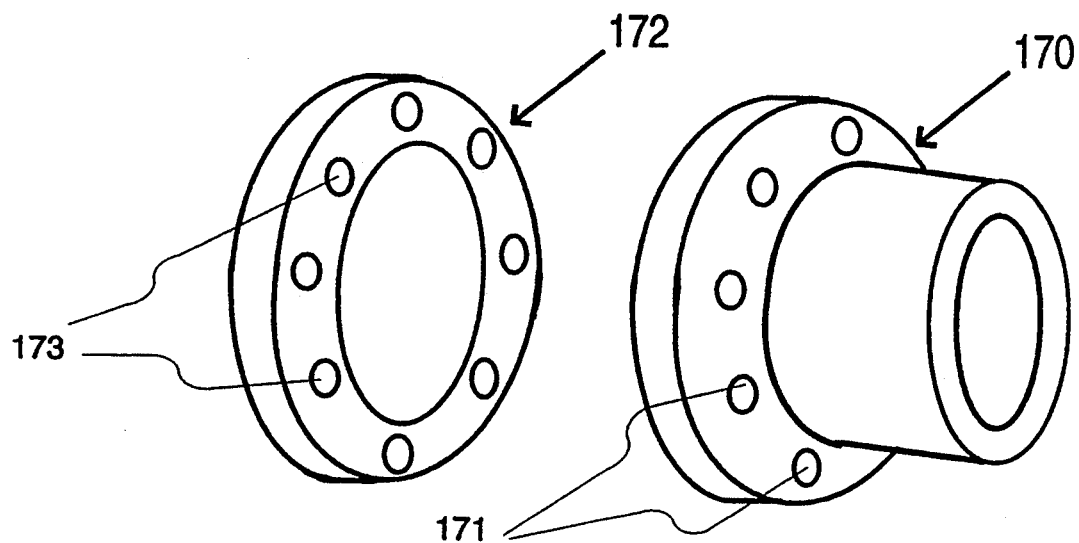
FIG. 14 shows an embodiment of an intake and/or exhaust connector of the present invention.

FIG. 14 shows a desirable embodiment of an intake or exhaust port that may be usefully employed with the flexible adsorber of the present invention. Flange 170 may be capable of being used to suspended the flexible adsorber from an overhead support, and may be attached to the top or sides of the absorber via a snap ring, adhesives, or by bolts, pins, snap connectors or screws through holes 171. A backing plate 172 may be employed, with holes 173 lined up to match holes 171 in flange 171. In this manner, a portion of a flexible side of the adsorber of the present invention may be sandwiched between backing plate 172 and flange 170; the user may apply such an intake/exhaust flange at any desired location(s) on the adsorber so as to customize the adsorber to the desired application at a particular site. Further, the material covering the inlet of flange 170 might not be cut away until the adsorber is first used on site. A threaded cap may also be used to cover a threaded flange before or after use to prevent material from spilling out. Multiple intake and exhaust flanges may be employed with any of the flexible adsorbers shown in the Figures.

Figure 15:
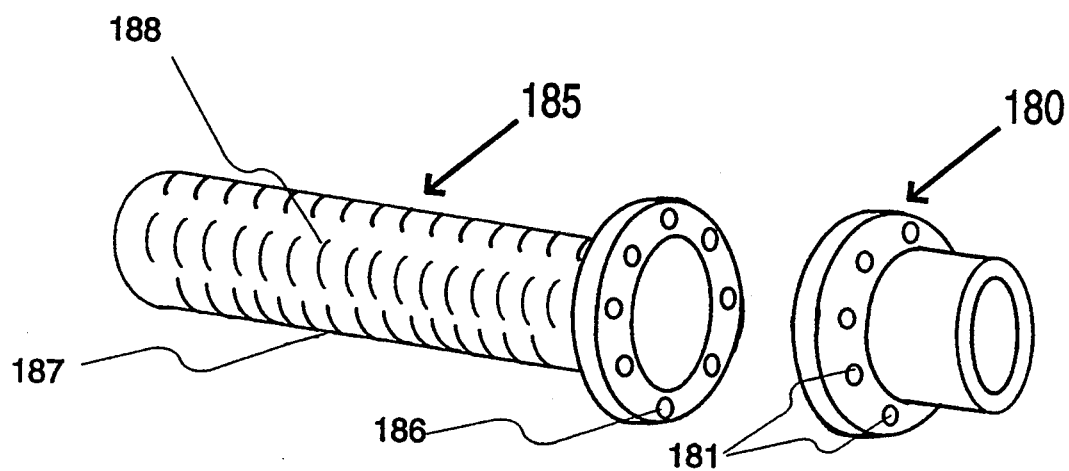
FIG. 15 shows an embodiment of a combination intake and/or exhaust connector and septa of the present invention.

FIG. 15 shows an intake or exhaust port equipped with a built in septum that may be usefully employed with the flexible adsorber of the present invention. Flange 180 may be attached to the top or sides of the absorber via a snap ring, adhesives, or by bolts, pins, snap connectors or screws through holes 181. A backing plate 185 may be employed, with holes 186 lined up to match holes 181 in flange 180. In this manner, the septum 187 (with slits 188 to permit vapor and liquid flow) can replace or supplement the mesh, screens or pallet structures otherwise used to permit contaminated materials to be exposed to a filter medium or adsorbent.

Figure 16:
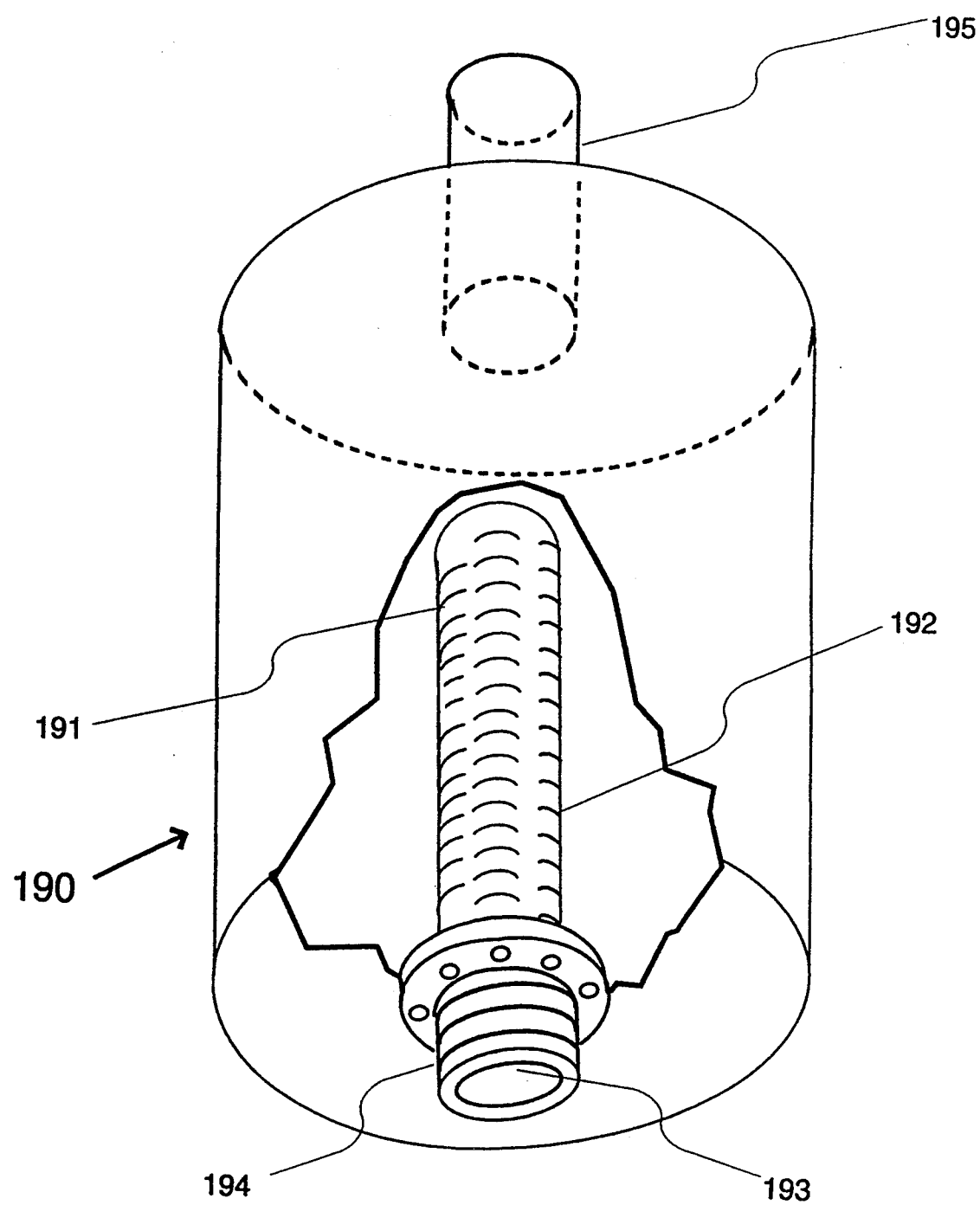
FIG. 16 shows a flexible adsorber with a threaded intake and septa of the present invention.

FIG. 16 shows bottom perspective view of flexible adsorber 190 mounted with a threaded intake and septa as shown in FIG. 15. Septum 191 (shown through the cutaway portion of flexible adsorber 190) is attached to the top (or bottom or sides) of the absorber via bolts. Slits 192 fluid to flow into the adsorbent bed. The intake end 193 of septum 191 may be configured with threads 194 to permit a seal with an fluid source, or to secure a cap (not shown) in place during storage or transport. Exhaust port 195 permits the purified effluent to exit the adsorber. Multiple septa may likewise be employed in the flexible adsorber of the present invention as shown in FIGS. 1-3, 4-7, 16 and others.

Figure 17:
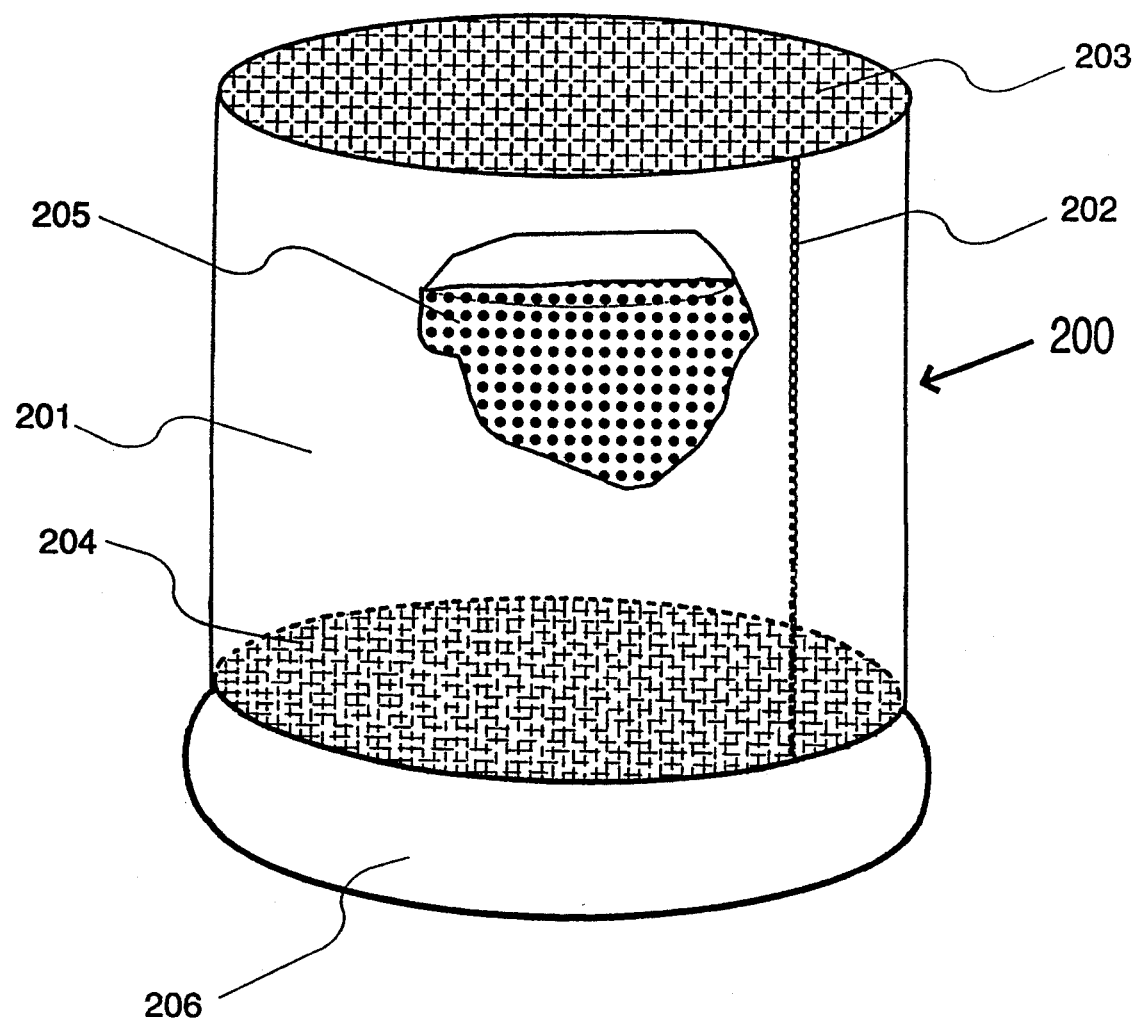
FIG. 17 shows a double mesh end flexible adsorber of the present invention.

FIG. 17 shows a double mesh end flexible adsorber 200 of the present invention. As with other cylinder-shaped flexible adsorbers shown in the Figures, a single rectangular sheet of material may be used to form cylinder wall 201, when opposite ends of the rectangular sheet are joined at seam 202. Mesh end 203 and mesh end 204 (end 204 being shown inside the adsorber) permit a fluid stream to enter the device, for exposure to filter medium 205. Flexible adsorbers may be cylindrical as shown in FIG. 17, or may be fabricated in any number of other useful shapes (cube, triangle, ball-shaped, and many others). The flexible sides (201 in FIG. 17) of the device permit it to be placed inside a tube as an "in line" filter, or sealingly placed over or adjacent to a contaminated stream. An inflatable, rubberized or otherwise flexible gasket/support seal 206 may assist in supporting the device, and in insuring that a seal is maintained so as to seal the device to the fluid source.

Figure 18:
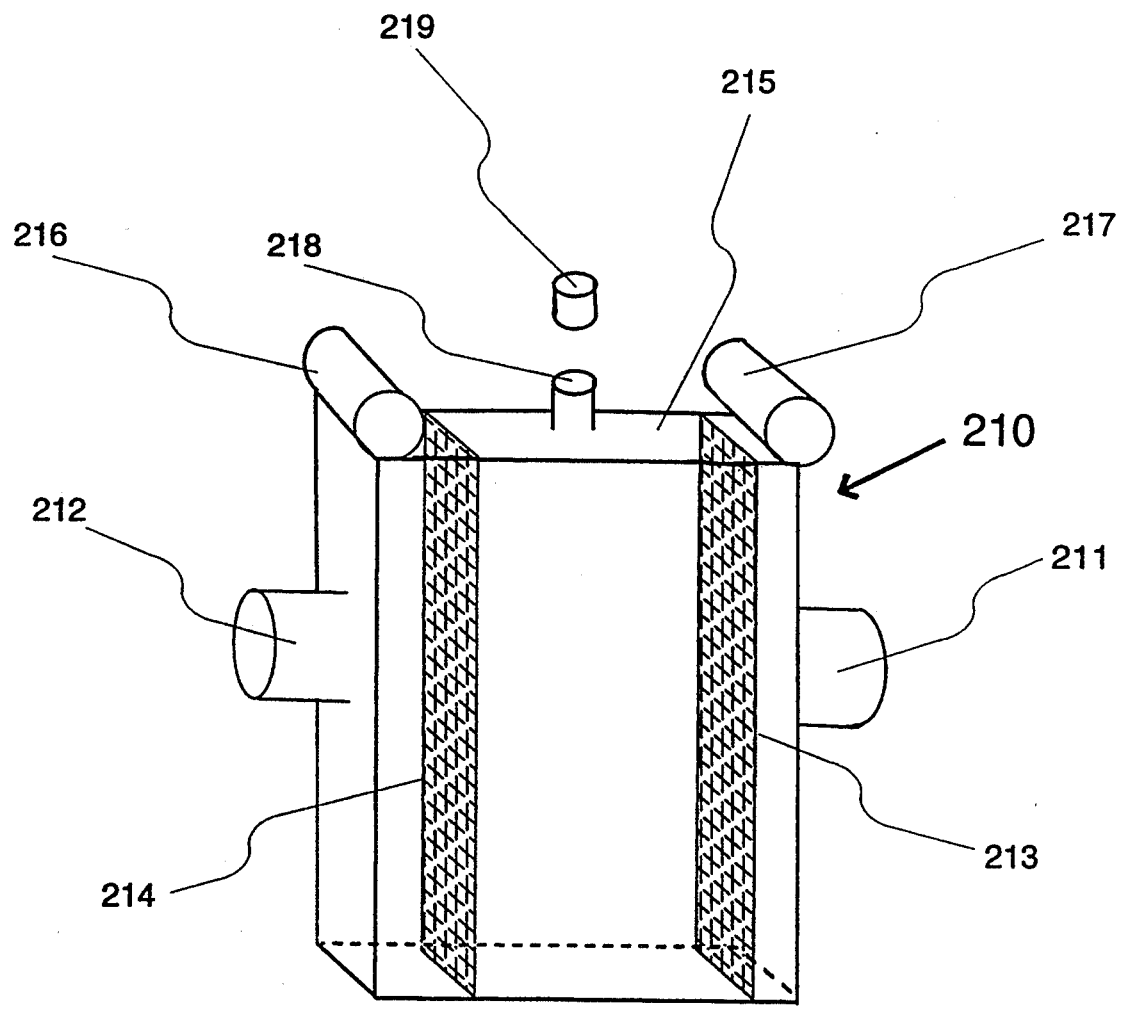
FIG. 18 shows a flexible adsorber with side intake/exhausts and a center adsorption chamber.

FIG. 18 shows a flexible adsorber with side intake/exhausts and a center adsorption chamber. Flexible adsorber 210 is equipped with side port 211 (intake or exhaust), side port 212 (intake or exhaust), and center adsorption chamber 215. Center adsorption chamber 215 contains the filter medium, which is held in place by screens 213 and 214. Filter pallets (such as those shown in FIGS. 5, 6, 9 and 11) may likewise be employed to position the filter medium. Floats 216 and 217 may be used to suspend the adsorber in a body of liquid, or the device may be hung from an overhead support (see FIGS. 1-3) or may rest on a lower surface (see FIGS. 5-8). Flexible adsorber 210 is shown equipped with an adsorbent/filter media fill port 218, which may be covered during operations, storage or transported with cap 219. The flexible adsorbers shown in FIGS. 1-8, 12, 13 and 16-20 may also include this fill port and cap feature.

Figure 19:
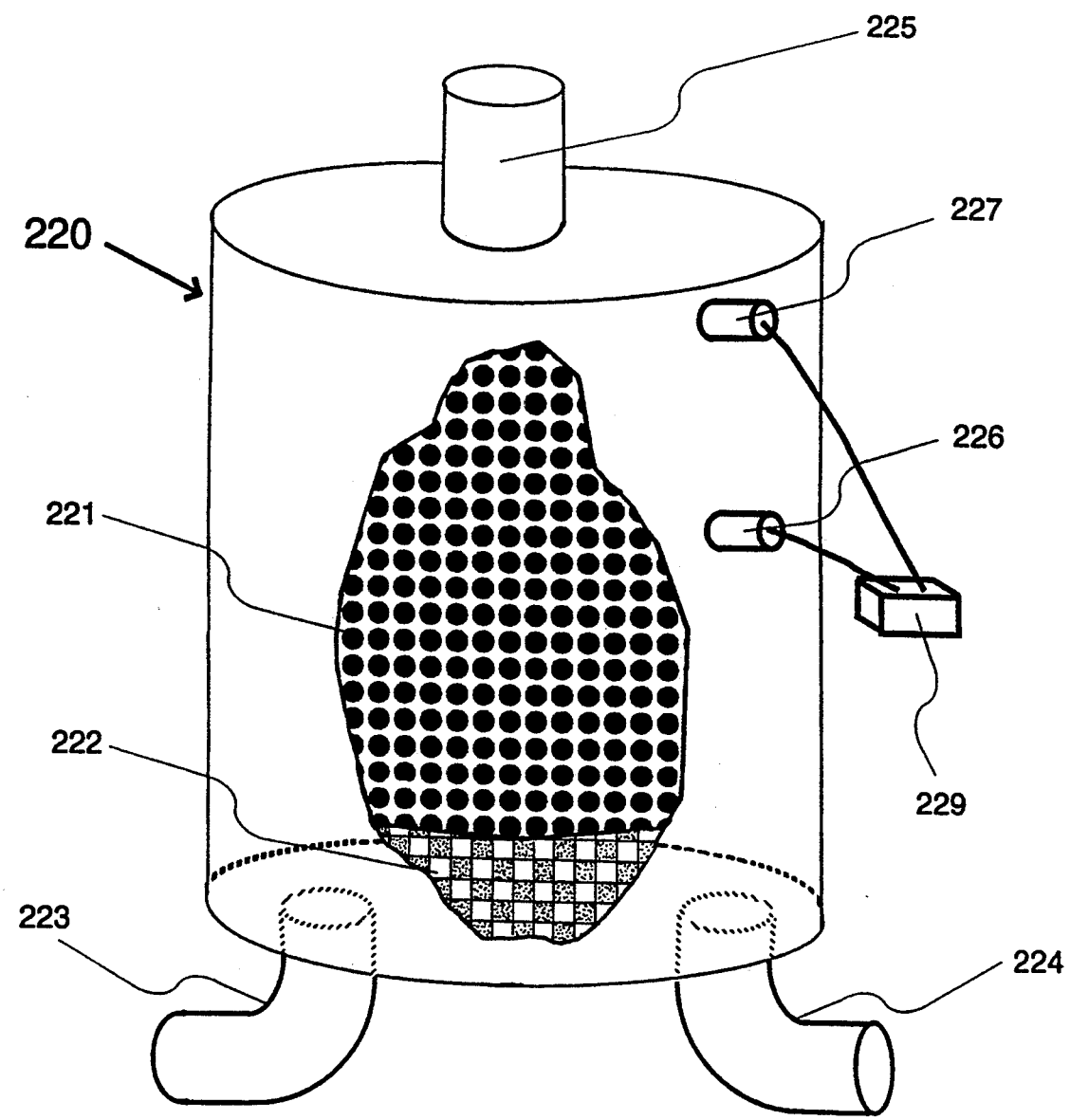
FIG. 19 shows a double intake flexible adsorber with multiple mesh-bagged adsorbent and multiple lower plenum spacers.

FIG. 19 shows a double intake flexible adsorber with multiple mesh-bagged adsorbent and multiple lower plenum spacers. Flexible adsorber 220 may be "freestanding," or may be suspended from an overhead support (see FIGS. 1-3). A plurality of small bundles of adsorbent are placed inside fluid-permeable bags 221. This plurality of adsorbent-filled bags may rest on a screen, a filter pallet, or a plurality of hollow spacers 222, so as the permit fluid flow-through from intake (or exhaust ports) 223 and 224. The contaminated fluid is filtered through the interlocking array of adsorbent-filled fluid-permeable bags 221, and flows out of (or into) the adsorber at port 225.

Provided the plurality of hollow spacers 222 are of structured with sufficiently fine pores, slots or spaces relative to the particulates or structure of the filter medium, these hollow spacers may also be employed in other embodiments of the present invention, and may replace the screen (FIGS. 1-3), filter pallet (FIGS. 5, 6, 9 and 11) or septa (FIGS. 15 and 16) as would be otherwise required. FIG. 19 also shows a first contamination detector 226 and second contamination detector 227, connected to an alarm/warning signal device 229. Contamination detector 226 may be employed to inform personnel or automatic monitoring equipment when the filter medium bed is nearly expended (in the case of upward fluid flow through the adsorber); contamination detector 227 (positioned above the level of the filter medium) may likewise be employed to inform personnel or automatic monitoring equipment when complete contaminated fluid breakthrough occurs. One or more contamination detectors can likewise be employed with the flexible adsorbers shown in FIGS. 1-3, 5-8, and others.

Figure 20:
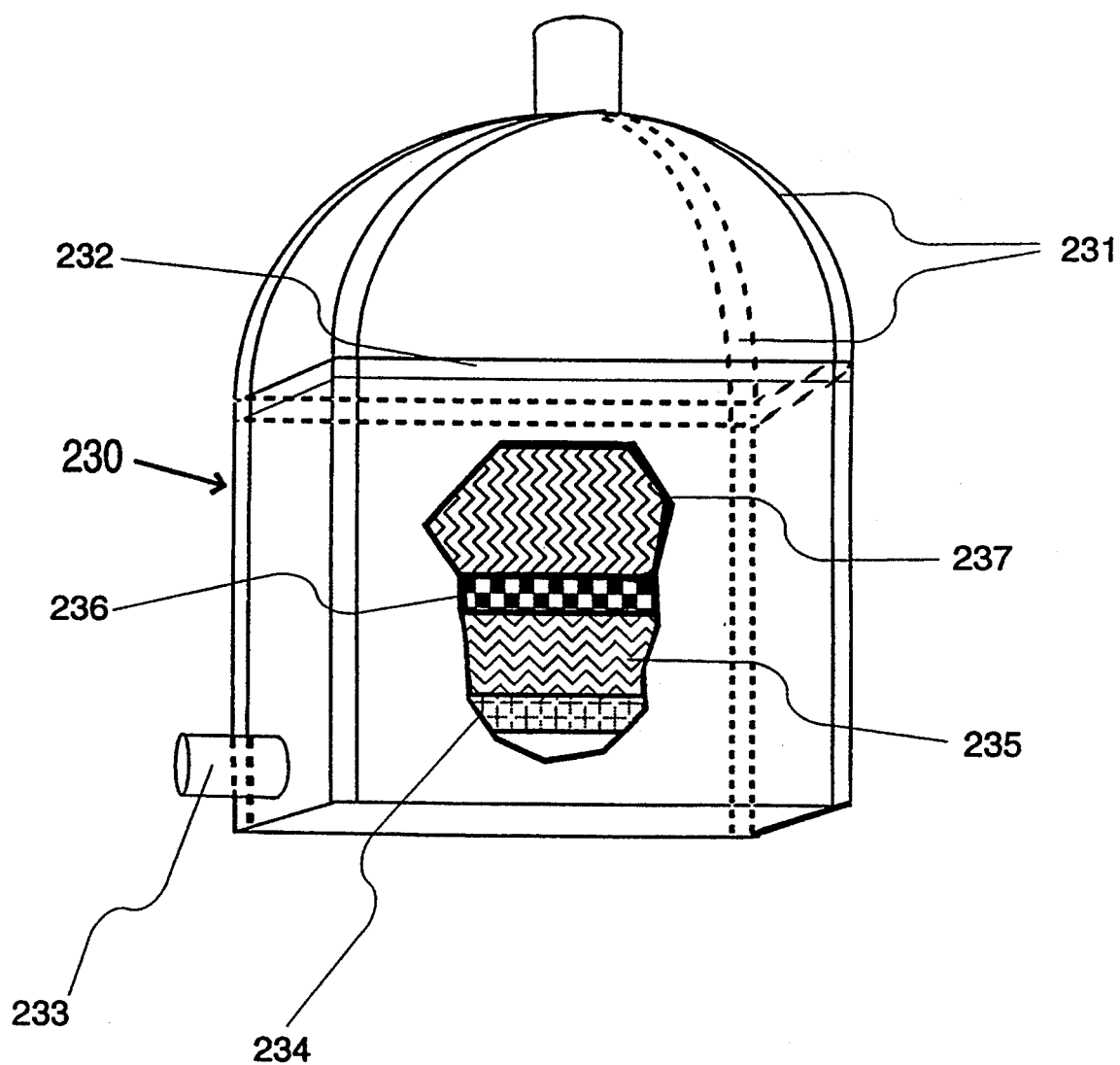
FIG. 20 shows a rib supported flexible adsorber with a side intake of the present invention.

FIG. 20 shows a rib supported flexible adsorber with a side intake, having multiple layers of filter media. Rib supports 231 position the outer walls of the adsorber in the desired shape and configuration; ribs 232 may optionally be employed to shape and support the walls of flexible adsorber 230 (as well as the flexible adsorbers shown in FIGS. 1-3, 5-8, and others). Side intake 233 permits the fluid to be filtered to flow through the first screen 234, for filtration by the first filter layer 235. Fluid then flows through the second screen 236, for filtration by the second filter layer 237; additional filtration layers can likewise be employed, and the direction of fluid flow through adsorber with flexible adsorber 230, and with the embodiments of the flexible adsorber shown in FIGS. 1-3, 5-8, and others. As with other embodiments of the present invention, it is possible to "back-flush" or otherwise cleanse the filter media by cycling a cleansing stream of vapor or liquid through the intake and/or exhaust ports of flexible adsorber 230.

Figure 21:
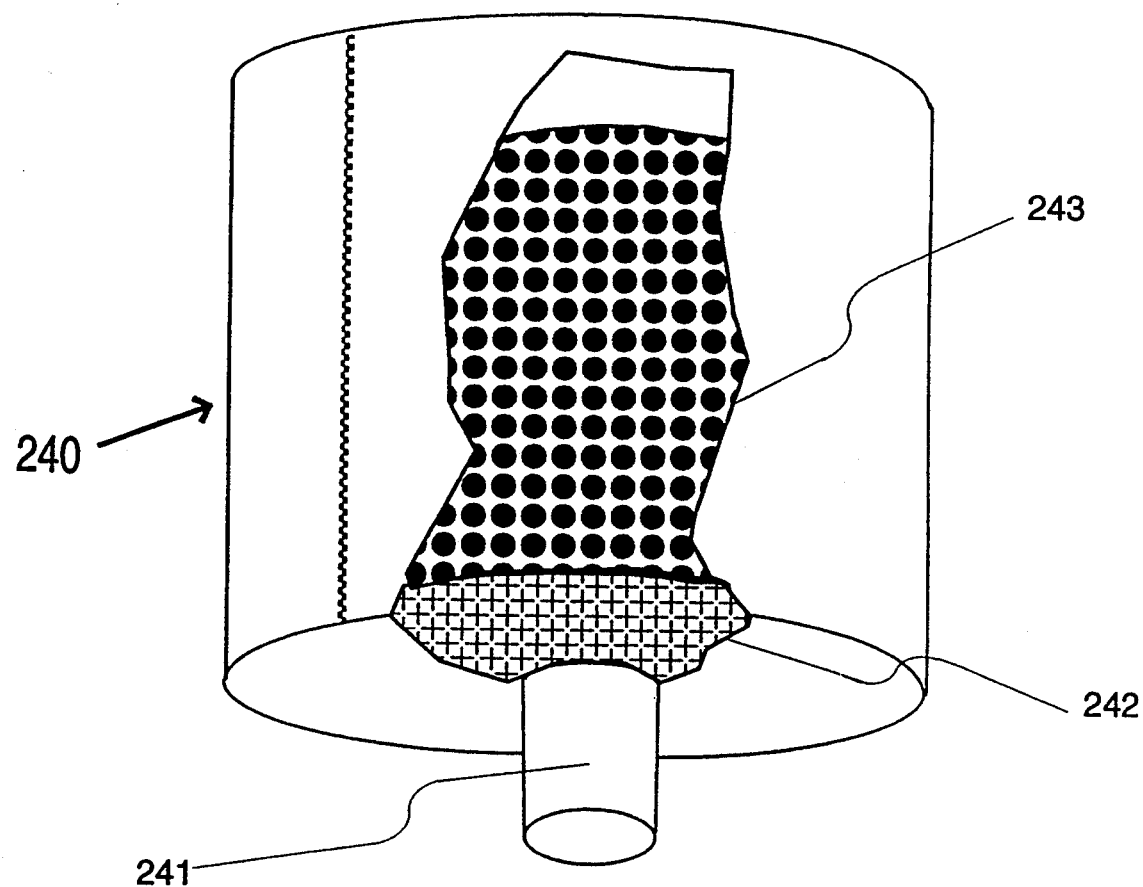
FIG. 21 shows a single-port flexible adsorber of the present invention.

FIG. 21 shows a flexible adsorber 240 having a single intake/exhaust port 241. A screen 242 is positioned adjacent to filter medium chamber 243. During a first "cycle," contaminated fluid is injected through the intake/exhaust port 241, the side walls of flexible adsorber 240 inflate, and the contaminated fluid is exposed to the filter medium. During a second "cycle," the fluid is withdrawn from the interior of the flexible adsorber 240, with contaminants remaining deposited on the filter medium. This embodiment may be configured with a mask so as to operate as a air filtration breathing bag. Larger versions of flexible adsorber 240 may be used to remove contaminants from a stream of gas or vapors as that stream is used to inflate and then deflate flexible adsorber 240. A filter pallet or other means of positioning the filter medium may likewise be used as shown in FIGS. 1-8 and 16-20. The filter medium in flexible adsorber 240 may be cleaned in situ by exposure to one or more cycles of a cleansing fluid.

The flexible adsorber of the present invention can be tailored according to the described embodiments to meet specific desired performance characteristics for any number of industrial, laboratory, field, floating, underwater and other applications. Although the flexible adsorbers of the present invention have been described in detail in the foregoing for purposes of illustration, it is to be understood that such details are solely for that purpose and that variations may be made therein by those skilled in the art without departing from the spirit and scope of the invention as described in the following claims.

What is claimed is:

1. A flexible-walled filter vessel comprising:
   a flexible bag having an external surface and a fluid impermeable internal surface, said flexible bag being operable to enclose at least one filter medium;
   at least one port in the flexible bag, said at least one port being operable to permit fluid streams to contact the filter medium;
   at least one fluid permeable support member operable to position the filter medium in the flexible bag and a filler port operable to access the at least one filter medium and a means for sealing said filler port.

2. A flexible-walled filter vessel comprising:
   a flexible bag having an external surface and a fluid impermeable internal surface, said flexible bag being operable to enclose at least one filter medium;
   at least one port in the flexible bag, said at least one port being operable to permit fluid streams to contact the filter medium; and
   at least one fluid permeable support member operable to position the filter medium in the flexible bag, said fluid permeable support member comprising an internal filter medium support pallet having at least one screen operable to position the filter medium.

3. The flexible-walled filter vessel as set forth in claim 1 or 2, or additionally comprising at least one means attached to the external surface of the flexible bag for hanging the filter vessel from an overhead support.

4. The flexible-walled filter vessel as set forth in claim 1 or 2, wherein the at least one port is operable to hang the filter vessel from an overhead support.

5. The flexible-walled filter vessel as set forth in claim 1 or 2, said filter vessel additionally comprising at least one substantially horizontal support strap attached to and substantially surrounding the external surface of the flexible bag.

6. The flexible-walled filter vessel as set forth in claim 1 or 2, said filter vessel additionally comprising at least one substantially vertical support strap attached to the external surface of the flexible bag, said vertical strap being operable to hang the filter vessel from an overhead support.

7. The flexible-walled filter vessel as set forth in claim 1 or 2, wherein the external surface additionally comprises a continuous loop of material operable to hang the filter vessel from an overhead support.

8. The flexible-walled filter vessel as set forth in claim 1 or 2, said filter vessel additionally comprising at least one rib operable to support the flexible bag.

9. The flexible-walled filter vessel as set forth in claim 1 or 2, wherein the at least one fluid permeable support member covers at least one port.

10. The flexible-walled filter vessel as set forth in claim 1 or 2, said filter vessel additionally comprising at least one buoyant means for supporting the filter vessel in a body of liquid.

11. The flexible-walled filter vessel as set forth in claim 1 or 2, said filter vessel additionally comprising a second port, said second port being operable to permit said fluid streams to continuously flow through the filter vessel.

12. The flexible-walled filter vessel as set forth in claim 1 or 2, whereby at least one filter medium comprises a porous adsorbent.

13. The flexible-walled filter vessel as set forth in claim 1 or 2, whereby at least one filter medium comprises activated carbon.

14. The flexible-walled filter vessel as set forth in claim 1 or 2, whereby the at least one permeable support member comprises a screen.

15. The flexible-walled filter vessel as set forth in claim 1 or 2, said filter vessel additionally comprising at least one pallet operable to support a lower portion of the filter vessel.

16. The flexible-walled filter vessel as set forth in claim 1 or 2, whereby the at least one permeable support member comprises an external filter media support pallet operable to position the filter medium, said external support pallet sealingly attached to the flexible bag.

17. The flexible-walled filter vessel as set forth in claim 1 or 2, said filter vessel additionally comprising at least one inflatable member operable to support a lower portion of the filter vessel.

18. The flexible-walled filter vessel as set forth in claim 1 or 2, said filter vessel additionally comprising a means for closing the at least one port, whereby the filter vessel serves as its own shipping container.

19. The flexible-walled filter vessel as set forth in claim 1 or 2, whereby the flexible bag is comprised of plastic.

20. The flexible-walled filter vessel as set forth in claim 1 or 2, whereby the flexible bag is comprised of a composite fabric.

21. The flexible-walled filter vessel as set forth in claim 1 or 2, whereby the impermeable internal surface of the flexible bag comprises a corrosion-resistant layer.

22. The flexible-walled filter vessel as set forth in claim 1 or 2, whereby the permeable support member comprises a corrosion-resistant layer.

* * * * *